(12) United States Patent
Weaver et al.

(10) Patent No.: US 9,017,685 B1
(45) Date of Patent: *Apr. 28, 2015

(54) PATHWAY FOR TH-17 CELL DEVELOPMENT AND METHODS UTILIZING SAME

(75) Inventors: Casey T. Weaver, Birmingham, AL (US); Paul R. Mangan, Doylestown, PA (US); Laurie E. Harrington, Birmingham, AL (US)

(73) Assignee: The UAB Research Foundation, Birmingham, AL (US)

( * ) Notice: Subject to any disclaimer, the term of this patent is extended or adjusted under 35 U.S.C. 154(b) by 86 days.

This patent is subject to a terminal disclaimer.

(21) Appl. No.: 12/580,870

(22) Filed: Oct. 16, 2009

Related U.S. Application Data

(63) Continuation of application No. 11/866,380, filed on Oct. 2, 2007.

(51) Int. Cl.
*A61K 39/395* (2006.01)
*C07K 16/18* (2006.01)

(52) U.S. Cl.
CPC ..................................... *C07K 16/18* (2013.01)

(58) Field of Classification Search
None
See application file for complete search history.

(56) References Cited

U.S. PATENT DOCUMENTS

| | | | |
|---|---|---|---|
| 5,981,483 A | 11/1999 | Dennis | |
| 6,800,735 B2 * | 10/2004 | Whitty et al. | 530/351 |
| 7,291,721 B2 * | 11/2007 | Giles-Komar et al. | 536/23.53 |
| 7,482,436 B2 | 1/2009 | Sugimura | |
| 7,790,862 B2 | 9/2010 | Lewis | |
| 7,807,160 B2 * | 10/2010 | Presta et al. | 424/133.1 |
| 2004/0156849 A1 * | 8/2004 | Gurney | 424/145.1 |
| 2006/0134113 A1 * | 6/2006 | Mihara | 424/145.1 |
| 2006/0140950 A1 * | 6/2006 | Cua et al. | 424/145.1 |
| 2007/0009518 A1 | 1/2007 | Novobrantseva | |
| 2007/0048315 A1 | 3/2007 | Presta | |

OTHER PUBLICATIONS

Kikly et al. 2006. Current Opinion in Immunology 18:670-675.*
Chen et al. 2006. J. Clin. Invest. 116:1317-1326.*
Harrington et al. 2005. Nature Immunology 6:1123-1132.*
Gabay 2006. Arthritis Research and Therapy 8(Suppl 2):1-6.*
Kaplanski et al. 2003. Trends in Immunology 24:25-29.*
Ohshima et al. 1998. PNAS. 95:8222-8226.*
Alonzi et al 1998. J. Exp Med. 187:461-468.*
Park, A distinct lineage of CD4 T cells regulates tissue inflammation by producing interleukin 17, Nature Immunol. Nov. 2005; 6(11): 1133-1141.
Tesmer, Th17 cells in human disease, Immunological Reviews 223: 87-113, 2008.
Veldhoen, TGFβ in the Context of an Inflammatory Cytokine Milieu Supports De Novo Differentiation of IL-17-Producing T Cells, Immunity 24, Feb. 2006, 179-189.
Mangan, Transforming growth factor-β induces development of the TH 17 lineage, Nature, May 11, 2006, 231-234, vol. 441.
Hori et al., *Science* 299:1057-1061.

* cited by examiner

*Primary Examiner* — Shulamith H Shafer
(74) *Attorney, Agent, or Firm* — Thomas G. Peterson; Bradley Arant Boult Cummings LLP

(57) ABSTRACT

The present disclosure demonstrates for the first time that Th-17 cells are the product of a distinct CD4⁺ T cell lineage with unique developmental and functional characteristics. The developmental signals required for Th-17 commitment and development are also described. As a result, the teachings of the present disclosure provide a basis for understanding the developmental pathway of Th-17 cells and offer novel avenues to modulate (stimulate or inhibit) this developmental program and offer new methods for the treatment and prevention of disease states and conditions related to aberrant activity of Th-17 cells.

5 Claims, 21 Drawing Sheets

PATHWAY FOR TH-17 CELL DEVELOPMENT AND METHODS UTILIZING SAME

CROSS-REFERENCE TO RELATED APPLICATIONS

This application is a continuation of U.S. application Ser. No. 11/866,380, filed Oct. 2, 2007, which is currently pending. U.S. application Ser. No. 11/855,380 cites the benefit of U.S. Provisional Application 60/848,670 under 35 U.S.C. §119, filed on Oct. 2, 2006.

STATEMENT AS TO FEDERAL FUNDING

The work described herein was supported by NIH Grants A1035783, A1057956 and DK64400. As such, the Federal Government has certain rights in this invention.

FIELD OF THE DISCLOSURE

The present disclosure is directed to CD4+ effector T cells in general. Specifically, the present disclosure relates to the description of a new CD4+ effector T cell termed Th-17, the development pathway for Th-17 development and methods of treatment and prevention for conditions characterized, at least in part, by Th-17 function.

BACKGROUND

The Th1/Th2 paradigm has provided the framework for understanding CD4+ T-cell biology and the interplay between innate and adaptive immunity for almost two decades. The adaptive immune responses are vital for the eradication of infectious agents, although dysregulated adaptive immune responses might also lead to autoimmune and chronic inflammatory diseases. A principal component of the adaptive immune response is the CD4$^+$ T cell, which can orchestrate the functional activity of both innate and adaptive immune systems. The directed differentiation of effector CD4$^+$ T cells by cytokines produced by pathogen-activated cells of the innate immune system provides a mechanism to coordinate the innate and adaptive immune responses for greatest host protection. Classically, effector CD4$^+$ T cells have been divided into two distinct lineages on the basis of their cytokine production profile: cells of the T helper (Th)1 lineage, which evolved to enhance eradication of intracellular pathogens (e.g. intracellular bacteria, viruses and some protozoa), are characterized by their production of interferon gamma (IFN-$\gamma$), a potent activator of cell-mediated immunity; and cells of the Th2 lineage, which evolved to enhance elimination of parasitic infections (e.g. helminths), are characterized by production of interleukin (IL)-4, IL-5, and IL-13, which are potent activators of B-cell immunoglobulin (Ig)E production, eosinophil recruitment and mucosal expulsion mechanisms (mucous production and hypermotility). Immune pathogenesis that results from dysregulated Th1 responses to self or commensal floral antigens can promote tissue destruction and chronic inflammation, whereas dysregulated Th2 responses can cause allergy and asthma.

Recent studies have defined a previously unknown arm of the CD4$^+$ T cell effector response, referred to as Th-17 cells, which is involved in immune regulation, immune pathogenesis and host defense. This knowledge has forced a reassessment of the Th1 lineage in autoimmunity and chronic inflammatory diseases. The cytokines IL-23 and IL-17, produced by Th-17 cells, have been linked to immune pathogenesis previously attributed to the Th1 lineage. However, the factors that specify differentiation of IL-17 effector cells from CD4$^+$ T-cell precursors are not understood. As a result, methods of treatment and prevention aimed at modulating the Th-17 developmental pathway and compositions for use in such methods have not been appreciated.

The present disclosure describes the development pathway of Th-17 cells, thereby offering novel insights on mechanisms to prevent and/or treat disease states and conditions associated with Th-17 function (either increased or decreased).

DETAILED DESCRIPTION

Definitions

Figure 1:
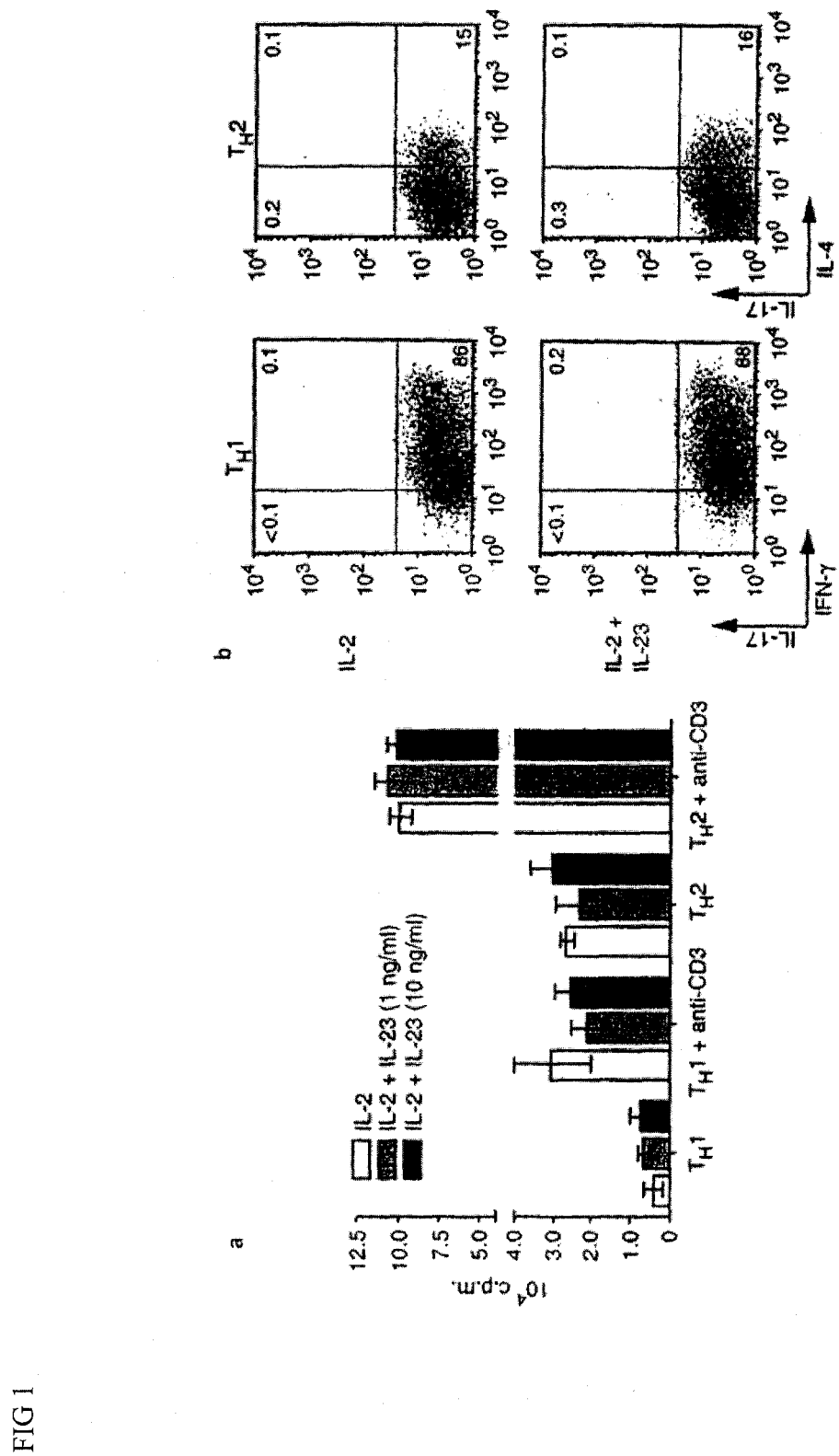
FIG. 1 illustrates that Th1 and Th2 cells are poorly responsive to IL-23.

The terms "prevention", "prevent", "preventing", "suppression", "suppress" and "suppressing" as used herein refer to a course of action (such as administering a compound or pharmaceutical composition) initiated prior to the onset of a symptom, aspect, or characteristics of a disease or condition so as to prevent or reduce such symptom, aspect, or characteristics. Such preventing and suppressing need not be absolute to be useful.

The terms "treatment", "treat" and "treating" as used herein refers a course of action (such as administering a compound or pharmaceutical composition) initiated after the onset of a symptom, aspect, or characteristics of a disease or condition so as to eliminate or reduce such symptom, aspect, or characteristics. Such treating need not be absolute to be useful.

The term "in need of treatment" as used herein refers to a judgment made by a caregiver that a patient requires or will benefit from treatment. This judgment is made based on a variety of factors that are in the realm of a caregiver's expertise, but that includes the knowledge that the patient is ill, or will be ill, as the result of a disease or condition that is treatable by a method or compound of the disclosure.

The term "in need of prevention" as used herein refers to a judgment made by a caregiver that a patient requires or will benefit from prevention. This judgment is made based on a variety of factors that are in the realm of a caregiver's expertise, but that includes the knowledge that the patient will be ill or may become ill, as the result of a disease or condition that is preventable by a method or compound of the disclosure.

The term "individual", "subject" or "patient" as used herein refers to any animal, including mammals, such as mice, rats, other rodents, rabbits, dogs, cats, swine, cattle, sheep, horses, or primates, and humans. The term may specify male or female or both, or exclude male or female.

The term "therapeutically effective amount" as used herein refers to an amount of a compound, either alone or as a part of a pharmaceutical composition, that is capable of having any detectable, positive effect on any symptom, aspect, or characteristics of a disease or condition. Such effect need not be absolute to be beneficial.

The term "Th-17", "Th-17 effector cell" and "IL-17 effector cell" as used herein refer to a CD4+ T cell that produces IL-17.

Introduction

Substantial advances have been made in understanding the developmental pathways that give rise to Th1 and Th2 cells (Murphy, Nat. Rev. Immunol., 2:933 (2002); Robinson, Immunity, 16:755 (2002); Szabo, Annu. Rev. Immunol., 21:713 (2003)). Th1 cell development is coupled to the sequential involvement of cell-extrinsic and cell-intrinsic factors, including signal transducer and transcription activator 1 (STAT1), the transcription factor T-bet, IL-12 and STAT4, whereas Th2 cell development is coupled to IL-4, STAT6 and the transcription factor GATA-3. Notably, cytokines produced by mature effector cells of each lineage can reinforce their own developmental program through positive and negative feedback acting on both naïve T cells and innate immune cells. Thus, IFN-γ produced by mature Th1 cells or innate immune cells, and IL-27, an IL-12 family member produced by innate immune cells, induce STAT1 signaling and T-bet expression in antigen-activated, naive CD4+ T cells, leading to up-regulation of the IL-12 receptor (IL-12R) on developing Th1 cells and suppression of GATA-3 (Szabo, J. Exp. Med., 185:817 (1997); Ouyang, Immunity, 9:745 (1998); Pflanz, Immunity, 16:779 (2002)). Similarly, IL-4 produced by mature Th2 cells initiates Th2 cell development through its up-regulation of GATA-3 via STAT6 and suppresses Th1 cell development by blocking IL-12R expression (Zheng, Cell, 89:587 (1997)). The ability of GATA-3 to promote its own transcription through a cell-intrinsic, positive feedback loop represents a potent mechanism for rapidly stabilizing Th2 cell development (Ouyang, Immunity, 12:27 (2000)). As a result of these robust counter-regulatory pathways, Th1 and Th2 cell development diverges rapidly after antigen priming to produce mature effector cells with stable, mutually exclusive expression of IFN-γ and IL-4, respectively.

Although immunopathology mediated by inappropriate or poorly controlled effector T cell responses has typically been viewed in the context of the Th1-Th2 paradigm, findings from two well established mouse models of autoimmunity have resulted in a paradigm shift. In both experimental autoimmune encephalomyelitis (EAE) and type II collagen-induced arthritis, two heretofore prototypical Th1 disease models, it has been found that IL-17-producing CD4+ effector T cells, not IFN-γ-producing effector cells, are pathogenic, thereby challenging the importance of classical Th1 cells in the induction and maintenance of autoimmune diseases and chronic inflammatory disease (Langrish, J. Exp. Med., 210:233 (2005); Cua, Nature, 421:744 (2003); Murphy, J. Exp. Med., 198:1951 (2003)). In both models, disease development is blocked in mice deficient in IL-23, which promotes the development of IL-17 effector cells (Aggarwal, J. Biol. Chem., 278:1910 (2003). In contrast, deficiency in IL-12, and thus IFN-γ effector cells, exacerbates disease development (Cua, Nature, 421:744 (2003); Murphy, J. Exp. Med., 198:1951 (2003); Gran, J. Immunol., 169:7104 (2002)). In EAE, adoptive transfer of IL-23-polarized IL-17 effector cells, but not IL-12 polarized Th1 effector cells, is required for disease (Langrish, J. Exp. Med., 210:233 (2005)). Those data have established the idea of a critical function for the IL-23-IL-17 pathway in at least some diseases previously thought to be mediated by IL-12 and/or IFN-γ and emphasize the importance of understanding the developmental origins of IL-17 effector cells.

While the art was aware of a subpopulation CD4+ T cells that produced IL-17, the differentiation pathway by which these cells developed was not defined. Because IL-23 and IL-12 share the common IL-12p40 subunit and interact with receptors that share the common IL-12Rβ1 submit, and because both IFN-γ and IL-17+ CD4+ T cells can be detected in diseased mice, it was proposed that there is considerable overlap between the developmental pathways that produce IFN-γ+ effector cells (Th1 cells) and IL-17+ effector cells (Th-17 cells) (Aggarwal, J. Biol. Chem., 278:1910 (2003); Bettelli, J. Exp. Med., 201:169 (2005); Oppman, Immunity, 13:715 (2000); Parham, J. Immunol., 13:715 (2002); Langrish, Immunol. Rev., 202:96 (2004)). In this model, both subsets of effector cells arise from a common Th1 precursor or pre-Th1-intermediate' that co-expresses the IL-12R and IL-23R. Accordingly, both IL-17 and IFN-γ effector subsets share a common early developmental program in which IFN-γ- or IL-27-activated induction of T-bet via STAT1 signaling is predicted to induce up-regulation of IL-12Rβ2 and IL-23R which pair with the constitutively expressed IL-12Rβ1 subunit to produce functional IL-12R and IL-23R, respectively (Bettelli, J. Exp. Med., 201:169 (2005); Parham, J. Immunol., 13:715 (2002); Lucas, Proc. Natl. Acad. Sci. USA, 100:15047 (2003); Hibbert, J. Interferon Cytokine Res., 23:513 (2003)). However, because expression of IL-17 and IFN-γ by individual effector T cells is for the most part mutually exclusive, this model predicts that the two pathways diverge contingent on signals associated with IL-12R or IL-23R stimulation on pre-Th1 intermediate cells (Langrish, J. Exp. Med., 210:233 (2005); Murphy, J. Exp. Med., 198:1951 (2003). However, an alternative model in which IL-17 and IFN-γ effector differentiation diverges earlier, perhaps at stage of the naive CD4+ T cells, leading to preferential expression of IL-12R or IL-23R is also possible. Support for the latter model has been confounded by the finding that activation of naive CD4+ precursor cells in the presence of IL-23 does not lead to substantial development of IL-17 effector cells (Langrish, J. Exp. Med., 210:233 (2005); Aggarwal, J. Biol. Chem., 278: 1910 (2003)). The role of Th-17 cells and the development thereof has recently been discussed (Weaver, Immunity, 24:677 (2006); Harrington, Curr. Opin. Immunol., 18:349 (2006)).

The present disclosure demonstrates for the first time that Th-17 cells are the product of a distinct CD4$^+$ T cell lineage with unique developmental and functional characteristics. The present disclosure describes the role of TGF-β and/or IL-6 as cytokines critical for the commitment of CD4$^+$ precursor cells, such as, but not limited to, naïve CD4+ T cells to Th-17 development and the role of IL-23 in reinforcing Th-17 development. The present disclosure demonstrates that the development of Th-17 cells is impaired in TGF-β deficient mice. The present disclosure also demonstrates that TGF-β up-regulates the expression of IL-23R, thereby conferring IL-23 responsiveness and priming such cells for further development under the influence of IL-23 and other factors to Th-17 effector T cells. Furthermore, the present disclosure also demonstrates that generation of functional Th-17 effector T cells was dependent on IL-23 but was independent of STAT1, T-bet, STAT4 and STATE. Furthermore, the Th1 effector cytokine IFN-γ and the Th2 effector cytokine IL-4 potently suppressed the development of the IL-17 effector cells from naive CD4$^+$ precursor cells, providing a mechanism by which the Th1 and Th2 developmental program antagonizes the Th-17 developmental program and contributes to lineage divergence. The present disclosure establishes that Th-17 cells develop via signaling pathways that are independent of those required for Th1 or Th2 cell development and that Th-17 cells are therefore the product of a distinct CD4$^+$T cell lineage with unique developmental and functional characteristics.

Therefore, the present disclosure provides the molecular basis for commitment and development of CD4$^+$ precursor cells to Th-17 effector cells in vivo and in vitro. Such an understanding provides a means to intervene in the pathway to modulate (either by increasing or decreasing) Th-17 commitment and development and subsequently the activity of Th-17 effector cells. As a result, the teachings of the present disclosure provide new methods for the treatment and prevention of disease state and conditions related to Th-17 function.

Methods of Treatment and Prevention

As disclosed herein, the present application discloses for the first time cells of the Th-17 lineage. The present disclosure thereby provides for methods of treatment and prevention whereby Th-17 function is inhibited. Such methods of treatment and prevention were not previously appreciated in the art as the art was not aware of a distinct Th-17 cell lineage. In one embodiment, the commitment, development, maintenance, survival and/or activity of a Th-17 cell is inhibited or stimulated. In a particular embodiment, Th-17 function may be stimulated through the actions of factors such as, but not limited to, TGF-β, IL-17, IL-23 and/or IL-6 on a CD4$^+$ precursor cell, such as, but not limited to, naïve CD4+ T cells, a CD4$^+$ precursor cell that has initiated or is committed to the Th-17 pathway or effector Th-17 cells. Therefore, Th-17 commitment, development, maintenance, survival and/or activity may be inhibited by blocking such stimulatory signals or stimulated by augmenting or providing such stimulatory signals. Furthermore, the present disclosure shows Th-17 commitment, development, maintenance, survival and/or activity may be inhibited through the actions of IFN-γ, IFN-α, IFN-β, IL-4 and/or IL-12 on a CD4$^+$ precursor cell and/or a CD4$^+$ precursor cell that has initiated or is committed to the Th-17 pathway. Therefore, Th-17 commitment, development, maintenance, survival and/or activity could by inhibited by providing and/or augmenting such inhibitory signals or stimulated by blocking such inhibitory signals.

The present disclosure describes methods to treat and prevent disorders that are related, at least in part, to Th-17 function. As used herein, a disorder is to be broadly defined and is meant to include, but not be limited to, defined disease states and other conditions that may or may not fall into an art recognized definition. In one embodiment, such disorders include autoimmune diseases, chronic inflammatory diseases, allograft rejection and/or conditions associated with the foregoing. As used herein the term "autoimmunity" or "autoimmune disease" means a condition caused by a malfunctioning immune system leading to self-attacks or self-stimulation of other body cells and/or tissues.

In such methods of treatment and/or prevention, the commitment, development, maintenance, survival and/or activity of the Th-17 cells is inhibited or stimulated, thereby leading to a decrease or an increase, respectively, in Th-17 function. Therefore, inhibiting/stimulating Th-17 function includes, but is not limited to, i) inhibiting/stimulating Th-17 commitment to a Th-17 developmental pathway (such as by inhibiting/stimulating the commitment of a CD4$^+$ precursor cell, such as, but not limited to, naïve CD4$^+$ T cells); ii) inhibiting/stimulating the development of a CD4$^+$ precursor cell that has initiated or is committed to the Th-17 developmental pathway; iii) inhibiting/stimulating the maintenance of a Th-17 phenotype (i.e., the production of IL-17); iv) inhibiting/stimulating the survival or Th-17 cells or a cell that has initiated or is committed to the Th-17 developmental pathway; and/or v) inhibiting/stimulating the activity of effector Th-17 cells. An increase or decrease in Th-17 function may include an increase or a decrease in the number of Th-17 cells present in a subject, an increase/decrease in the maintenance of the Th-17 phenotype, an increase/decrease in the survival of Th-17 cells, an increase or a decrease in the activity of the Th-17 cells (including activity induced by cytokines, growth factors and other agents secreted by Th-17 cells) that are present in a combination of the foregoing.

Th-17 function may be inhibited by blocking signals that stimulate Th-17 commitment, development, maintenance, survival and/or activity; such signals include, but are not limited to, TGF-β, IL-6, IL-17 and/or IL-23. Furthermore, Th-17 function may be inhibited by providing and/or augmenting signals that inhibit Th-17 commitment, development, maintenance, survival and/or activity; such signals include, but not limited to IFN-γ, IFN-α, IFN-β, IL-4 and/or IL-12. In certain embodiment, such signals stimulate the development of cells of the Th1 and/or Th2 lineage.

Conversely, Th-17 function may be stimulated by blocking signals that inhibit Th-17 commitment, development, maintenance, survival and/or activity; such signals include, but are not limited to, IFN-γ, IFN-α, IFN-β, IL-4 and/or IL-12. In certain embodiment, such signals stimulate the development of cells of the Th-1 and/or Th-2 lineage. Furthermore, Th-17 function may be stimulated by providing and/or augmenting signals that stimulate Th-17 the commitment, development, maintenance, survival and/or activity; such signals include, but are not limited to, TGF-β, IL-6, IL-17 and/or IL-23. Other factors that stimulate or inhibit Th-17 function are known in the art and described in Harrington et al., Current Opinion in Immunology, 18, 349-356 2006 and Weaver et al., Immunity, 24, 677-688 2006.

Such methods of treatment and prevention were not previously appreciated in the art and are made possible by the teachings of the present disclosure regarding the existence and developmental program of Th-17 cells.

In one embodiment, the teachings of the present disclosure provide for the treatment or prevention of a disorder that is characterized, at least in part, by increased or aberrant Th-17 function. In one embodiment, such disease states, disorders and conditions include, but are not limited to, autoimmunity, chronic inflammatory disease, allograft rejection and/or conditions associated with therewith. Such disease states, disorders and/or conditions associated with therewith include, but are not limited to, acute disseminated encephalomyelitis, alopecia areata, ankylosing spondylitis Addison's disease, antiphospholipid antibody syndrome, aplastic anemia, arthritis, autoimmune hemolytic anemia, autoimmune hepatitis, Behcet's disease, bullous pemphigoid, cardiomyopathy, celiac sprue-dermatitis, chronic fatigue immune dysfunction syndrome, chronic obstructive pulmonary disease, cicatricial pemphigoid, CREST syndrome, cold agglutinin disease, coeliac disease, Crohn's disease, diabetes mellitus (type 1), encephalitis, fibromyalgia-fibromyositis, Goodpasture's syndrome, Graves' disease, Guillain-Barré syndrome, Hashimoto's disease, idiopathic thrombocytopenic purpura, idiopathis pulmonary fibrosis, IgA nephropathy, inflammatory, inflammatory bowel disease, demyelinating polyneuropathy, juvenile arthritis, lupus erythematosus, Meniere's disease, multiple sclerosis, myasthenia gravis, opsoclonus myoclonus syndrome, optic neuritis, Ord's thyroiditis, pemphigus, pernicious anemia, primary biliary cirrhosis, psoriasis, psoriatic arthritis. Raynaud's phenomenon, rheumatic fever, rheumatoid arthritis, Reiter's syndrome, Sjögren's syndrome, sarcoidosis, scleroderma, stiff-man syndrome, Takayasu's arteritis, temporal arteritis, warm autoimmune hemolytic anemia, ulcerative colitis, uveitis, vasculitis, vitiligo and Wegener's granulomatosis.

Furthermore, an increased or aberrant Th-17 function has recently been linked to allograft rejection and/or conditions associated therewith. Allograft rejections are defined herein as a graft of an organ and/or tissue obtained from a donor of the same species as, but with a different genetic make-up from, the recipient. Therefore, allograft rejection is commonly encountered in subjects subject to solid organ and/or hematopoietic transplantation. Solid organ transplantation includes, but is not limited to, transplantation of the liver, heart, kidney and/or pancreatic islets. Hematopoietic transplantation includes, but is not limited to, bone marrow and stem cell engraftment.

The method of treatment comprises the steps of identifying a subject in need of such treatment and initiating in said subject a treatment regimen that decreases Th-17 function. In one embodiment, the method of treatment comprises inhibiting the commitment to a Th-17 developmental pathway (such as by inhibiting the commitment of a CD4$^+$ precursor cell, such as, but not limited to, naïve CD4$^+$ T cells); ii) inhibiting the development of a precursor cell that has initiated or is committed to the Th-17 developmental pathway; iii) inhibiting the maintenance of a Th-17 phenotype (i.e., the production of IL-17); iv) inhibiting the survival of Th-17 effector cells or a cell that has initiated or is committed to the Th-17 developmental pathway; and/or v) inhibiting the activity of effector Th-17 cells. In a specific embodiment, the methods of treatment comprise administering to a subject in need of such treatment a therapeutically effective amount of an antagonist of Th-17 function that inhibits at least one of the commitment, development, maintenance, survival or activity of the Th-17 effector cell thereby reducing the Th-17 effector cell activity. Such antagonist may inhibit, directly or indirectly, the activity of an agent that stimulates the commitment, development, maintenance, survival or activity of the Th-17 effector cell, such as but not limited to, TGF-β, IL-6, IL-17 and/or IL-23. Such antagonist may also inhibit, directly or indirectly the action of gene or polypeptide that is required or beneficial for the commitment, development, maintenance, survival or activity of the Th-17 effector cell. Furthermore, such antagonist may inhibit, directly or indirectly, the commitment, development, maintenance, survival or activity of the Th-17 effector cell (such as by blocking the activity of an inhibitory factor, such as but not limited to IFN-γ or IL-4).

The method of prevention comprises the steps of identifying a subject in need of such prevention and initiating in said subject a treatment regimen that decreases Th-17 function. In one embodiment, the method of prevention comprises i) inhibiting the commitment to a Th-17 developmental pathway (such as by inhibiting the commitment of a CD4$^+$ precursor cell, such as, but not limited to, naïve CD4$^+$ T cells); ii) inhibiting the development of a precursor cell that has initiated or is committed to the Th-17 developmental pathway; iii) inhibiting the maintenance of a Th-17 phenotype (i.e., the production of IL-17); iv) inhibiting the survival of Th-17 effector cells or a cell that has initiated or is committed to the Th-17 developmental pathway; and/or v) inhibiting the activity of effector Th-17 cells. In a specific embodiment, the methods of prevention comprise administering to a subject in need of such treatment a therapeutically effective amount of an antagonist of Th-17 function that inhibits at least one of the commitment, development, maintenance, survival or activity of the Th-17 effector cell thereby reducing the Th-17 effector cell activity. Such antagonist may inhibit, directly or indirectly, the activity of an agent that stimulates the commitment, development, maintenance, survival or activity of the Th-17 effector cell, such as but not limited to, TGF-β, IL-6, IL-17 and/or IL-23. Such antagonist may also inhibit, directly or indirectly the action of gene or polypeptide that is required or beneficial for the commitment, development, maintenance, survival or activity of the Th-17 effector cell or stimulate the action of a gene or polypeptide that is detrimental to the commitment, development, maintenance, survival or activity of the Th-17 effector cell. Furthermore, such antagonist may inhibit, directly or indirectly, the commitment, development, maintenance, survival and/or activity of the Th-17 effector cell.

The antagonist for use in the methods of treatment and prevention may be a small molecule, a pharmaceutical, a specific antagonist of the signaling pathways for such stimulatory or inhibitory signals or for signaling pathways generated thereby, a non-coding RNA, an antisense nucleotide, an oligopeptide, or an antibody or portions thereof. Such antagonist may be provided as a pharmaceutical composition in a pharmaceutically acceptable carrier as described herein. In a specific embodiment, the antagonist is administered in a therapeutically effective amount. Such administration would thereby treat the disorder that is characterized, at least in part, by increased or aberrant Th-17 function. As discussed above, the treatment/prevention need not be absolute to provide benefit in the methods disclosed.

As discussed above, antagonists of the Th-17 may be used in methods to treat and prevent disorders that are characterized, at least in part, by an increased or aberrant Th-17 function. As such, antagonists of Th-17 function are provided; such antagonist may act by inhibiting the commitment, development, maintenance, survival and/or activity of the Th-17 effector cell. Such antagonists encompass those that act by inhibiting, directly or indirectly, the activity of agents that stimulate Th-17 commitment, development and/or activity, such as for example, by blocking stimulatory signals (for example, an anti-IL-6 antibody or an anti-IL-6R antibody). Such antagonists also encompass those that act by inhibiting, directly or indirectly, the commitment, development, maintenance, survival and/or activity of the Th-17 effector cell, such as, for example, decreasing commitment of CD4$^+$ precursor cells to Th-17 cells (such as for example, IL-4 or an agent that mimics the activity of IL-4). Such antagonists further encompass those agents that inhibit, in whole or in part, the activity of genes and/or polypeptides specific to Th-17 function (those factors expressed in Th-17 cells, but not in or at reduced levels in Th-1, Th-2 or Th-1 and Th-2 cells). Examples of such proteins specific to Th-17 function are discussed herein (see Table 1 below). Factors that stimulate Th-17 function are discussed herein and known in the art and include, but are not limited to, TGF-β, IL-6, IL-17 and IL-23; factors that inhibit Th-17 function are discussed herein and known in the art and include, but are not limited to, IFN-γ, IFN-α, IFN-β, IL-4 and/or IL-12. Such antagonists are useful, for example, for (i) treating and/or preventing disease states that are characterized, at least in part, by an increased or aberrant Th-17 function; (ii) modulating the developmental pathway of Th-17 cells as described herein; and (iii) modulating the production of various cytokines and other signaling molecules produced by Th-17 cells or a cell that has initiated and/or is committed to the developmental pathway to produce a Th-17 cell.

In one embodiment, an antagonist of the commitment, development, maintenance, survival and/or activity of a Th-17 effector cell is an antibody directed to a factor that stimulates Th-17 function or an antibody directed to a receptor for such factor. In one embodiment, the antibody is a blocking antibody that fully or partially blocks the interaction of the given factor with its receptor, whether the antibody is directed to the particular factor (for example, IL-6) or to a receptor for that factor (for example, the IL-6 receptor). In an alternate embodiment, the antibody is directed against the receptor for the factor and binds to the extracellular ligand binding domain of such receptor. Such antibody may block the activation of the receptor (as for an agent that stimulates Th-17 development, commitment and/or activity) or such antibody may stimulate the activity of such receptor (as for an agent that blocks Th-17 commitment, development and/or activity). As used herein, the term "antibody" is used in the broadest sense and specifically covers monoclonal antibodies (including antagonist, e.g. neutralizing antibodies and agonist antibodies as discussed below), polyclonal antibodies, multi-specific antibodies (e.g., bispecific antibodies), as well as antibody fragments. Specifically included are "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see for example, U.S. Pat. No. 4,816,567; Morrison et al., Proc. Natl. Acad. Sci. USA, 81:6851-6855, 1984). The monoclonal antibodies further include "humanized" antibodies or antibody fragments thereof (such as, but not limited to, Fv, Fab, Fab', F(ab)$_2$ or other antigen-binding subsequences of antibodies) which contain minimal sequence derived from non-human immunoglobulin. For the most part, humanized antibodies are human immunoglobulins (recipient antibody) in which residues from a complementarity determining region (CDR) of the recipient are replaced by residues from a CDR of a non-human species (donor antibody) such as mouse, rat or rabbit having the desired specificity, affinity, and capacity. In some instances, Fv framework (FR) residues of the human immunoglobulin are replaced by corresponding non-human residues. Furthermore, humanized antibodies may comprise residues which are found neither in the recipient antibody nor in the imported CDR or FR sequences. These modifications are made to further refine and maximize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin sequence. The humanized antibody may also comprise at least a portion of an immunoglobulin constant region (Fc), typically that of a human immunoglobulin. "Antibody fragments" comprise a portion of an intact antibody, preferably the antigen binding or variable region of the intact antibody. Examples of antibody fragments include Fab, Fab', F(ab')$_2$, and Fv fragments, diabodies, linear antibodies (Zapata et al., Protein Eng. 8(10):1057-1062, 1995), single-chain antibody molecules and multi-specific antibodies formed from antibody fragments.

In an alternate embodiment, an antagonist of the commitment, development, maintenance, survival and/or activity of a Th-17 effector cell is an oligopeptide that binds to a particular factor or a receptor for such factor. Such an oligopeptide may block the action of such factor, either by binding the factor itself of the receptor for such factor. In one embodiment, an oligopeptide binds to the extracellular ligand binding domain of the receptor. Oligopeptides may be chemically synthesized using known oligopeptide synthesis methodology or may be prepared and purified using recombinant technology. Such oligopeptides are usually at least about 5 amino acids in length, alternatively at least about 10, 25, 50, 75 or 100 amino acids in length. Such oligopeptides may be identified without undue experimentation using well known techniques. In this regard, it is noted that techniques for screening oligopeptide libraries for oligopeptides that are capable of specifically binding to a polypeptide target are well known in the art (see, for example, U.S. Pat. Nos. 5,556,762, 5,750,373, 4,708,871, 4,833,092, 5,223,409, 5,403,484, 5,571,689, 5,663,143; PCT Publication Nos. WO 84/03506 and WO84/03564; Geysen et al., Proc. Natl. Acad. Sci. U.S.A., 81:3998-4002 (1984); Geysen et al., Proc. Natl. Acad. Sci. USA, 82:178-182 (1985); Geysen et al., in Synthetic Peptides as Antigens, 130-149 (1986); Geysen et al., J. Immunol. Meth., 102:259-274 (1987); Schoofs et al., J. Immunol., 140:611-616 (1988), Cwirla, S. E. et al. (1990) Proc. Natl. Acad. Sci. USA, 87:6378; Lowman, H. B. et al. (1991) Biochemistry, 30:10832; Clackson, T. et al. (1991) Nature, 352: 624; Marks, J. D. et al. (1991), J. Mol. Biol., 222:581; Kang, A. S. et al. (1991) Proc. Natl. Acad. Sci. USA, 88:8363, and Smith, G. P. (1991) Current Opin. Biotechnol., 2:668). In certain embodiments, an oligopeptide may be conjugated to a cytotoxic agent or a diagnostic agent; such agents are well known in the art, as well as methods of conjugating such agents with oligopeptides.

In yet another alternate embodiment, an antagonist of the commitment, development, maintenance, survival and/or activity of a Th-17 effector cell is an organic molecule that binds to a Th-17 stimulating factor or a receptor for such factor (other than an oligopeptide or antibody as described above). In certain case, the organic molecule may block the activity of those agents that stimulate Th-17 function (as in the case of a compound that binds to IL-6 and prevents its interaction with the IL-6 receptor or a compound that binds to but does not activate or fully activate a receptor for a factor that is involved inhibiting Th-17 function); alternatively, the organic molecule may provide, augment or stimulate the activity of those agents that inhibit Th-17 function (as in the case of a compound that binds to the IL-4 receptor and stimulates, either in whole or in part the activity of such receptor). An organic molecule may be, for example, a pharmaceutical compound or an organic chemical compound. Such an organic molecule may be identified and chemically synthesized using known methodology (see, e.g., PCT Publication Nos. WO00/00823 and WO00/39585). Given the teachings of the prior art, such organic molecules may be identified without undue experimentation using well known techniques. In certain embodiments, an organic molecule may be conjugated to a cytotoxic agent or a diagnostic agent; such agents are well known in the art, as well as methods of conjugating such agents with oligopeptides.

In a further embodiment, an antagonist of the commitment, development, maintenance, survival and/or activity of a Th-17 effector cell is a soluble form of the receptor, or portion thereof, for a specific factor (for example, a soluble form of the IL-6 receptor that is not membrane bound that blocks IL-6 activity; in some cases soluble antibody may also be stimulatory for such factor, as is the case for the soluble IL-4 receptor, see U.S. Pat. No. 6,063,371). Such soluble forms of the receptors may compete with membrane-bound forms of the receptor for binding to the Th-17 stimulating factor. The soluble form of the receptor may comprise all of the extracellular domain of the receptor or a ligand-binding portion of the extracellular domain of the receptor. In certain cases, the soluble form of the receptor may lack all or a portion of the transmembrane domain. The determination of the ligand-binding portion may be determined by methods that are well known in the art. Soluble forms of the receptors for Th-17 stimulating factors have been described (see, for example, US Publication Nos. 2005/0013814 for a description of a soluble form of the IL-17 receptor; 2005/0208052 for a description of a soluble form of the IL-23 receptor; 2007/0172455 for a description of a soluble form of the IL-6 receptor; 2001/0053764 and 2005/0171337 for a description of a soluble form of the IL-1 receptor; 2002/0052475 for a description of a soluble form of the IL-18 receptor; and 2003/012521 for a description of a soluble form of the TGF-β receptor).

In still a further embodiment, an antagonist of the commitment, development, maintenance, survival and/or activity of a Th-17 effector cell is a polynucleotide, such as, but not limited to, an antisense nucleic acid that decreases expression of a Th-17 stimulating factor or a receptor for such factor. A decrease in expression may include a decrease in transcription of the gene and/or translation of the mRNA. An antisense nucleic acid may bind to a nucleic acid (DNA or RNA) encoding a Th-17 stimulating factor or a receptor for such factor. Such antisense nucleic acid may be an oligonucleotide of about 10-30 nucleotides in length. Such antisense oligonucleotide may comprise modified sugar-phosphodiester backbones or other sugar linkages, such as but not limited to phosphorothioate linkages and linkages as described in WO 91/06629. In a particular embodiment, the antisense nucleic acid is a short interfering RNA, a micro RNA, a short hairpin RNA or other RNA species that mediates RNA interference. The use of such techniques to regulate cytokine expression has been described (see US Publication Nos: 2005/0261219, 2005/0182007 and 2005/0143333). Also included are polynucleotides and other factors that increase the expression of factors that inhibit Th-17 function.

In yet a further embodiment, an antagonist of the commitment, development, maintenance, survival and/or activity of a Th-17 effector cell is an agent that itself directly or indirectly inhibits Th-17 commitment, development and/or activity. Exemplary agents are IFN-γ, IFN-α, IFN-β, IL-4 and/or IL-12. Furthermore, antagonists also include agents that augment of mimic the activity of IFN-γ, IFN-α, IFN-β, IL-4 and/or IL-12 (such as an antibody that stimulates a receptor for IFN-γ, IFN-α, IFN-β, IL-4 and/or IL-12).

The present disclosure describes methods to treat and prevent disorders that are characterized, at least in part, by decreased Th-17 function. In one embodiment, disorders include, but are not limited to, bacterial and fungal infections and/or conditions associated therewith. Although the pathogenic potential of Th-17 action has been discussed above, Th-17 cells play a role in the control of certain classes of pathogens, analogous to the function of Th1 and Th2 cell for controlling intracellular pathogens and parasites, respectively. Il-23 and IL-17 (products of Th-17 cells), have been associate with host protection in a growing number of bacterial infection models, such as, but not limited to, *Klebsiella pneumonia, Borrelia burgdorferi, Bordetella pertussis* and *Citrobacter rodentium*. Furthermore, TGF-β is an inductive factor in antibody isotype switching from IgA to IgG2b immunoglobulin subclasses. Such a switch favors antibody production that is targeted to Fc receptors on phagocytic cells which is crucial for phagocytic clearance of extracellular bacteria. In such methods of treatment and/or prevention, the function of Th-17 cells is stimulated thereby leading to an increase in the commitment, development, maintenance, survival and/or activity of a Th-17 effector cell. Such methods of treatment and prevention were not previously appreciated in the art and are made possible by the teachings of the present disclosure regarding the existence and developmental program of Th-17 cells.

In one embodiment, the teachings of the present disclosure provide for the treatment of a disorder that is characterized, at least in part, by decreased or aberrant Th-17 function. In one embodiment, such disorders include, but are not limited to, bacterial and fungal infections and/or conditions associated therewith. Specifically, such bacterial infections may be caused, at least in part, by *Klebsiella pneumonia, Borrelia burgdorferi, Bordetella pertussis* and enteropathogenic *Escherichia coli* (the human equivalent of infection with *Citrobacter rodentium*), fungi and those organisms not cleared by Th1 and Th2 responses.

The method of treatment comprises the steps of identifying a subject in need of such treatment and initiating in said subject a treatment regimen that increases Th-17 function. In one embodiment, the number of Th-17 cells in a subject is increased; in an alternate embodiment, the activity of at least some Th-17 cells in a subject is increased; in yet another alternate embodiment, the number of Th-17 cells and the activity of at least some Th-17 cells in the subject are increased. In one embodiment, the methods of treatment comprise administering to a subject in need of such treatment at least one Th-17 agonist.

The method of treatment comprises the steps of identifying a subject in need of such treatment and initiating in said subject a treatment regimen that increases Th-17 function. In one embodiment, the method of treatment comprises i) stimulating the commitment to a Th-17 developmental pathway (such as by stimulating the commitment of a CD4$^+$ precursor cell, such as, but not limited to, naïve CD4$^+$ T cells); ii) stimulating the development of a precursor cell that has initiated or is committed to the Th-17 developmental pathway; iii) stimulating the maintenance of a Th-17 phenotype (i.e., the production of IL-17); iv) stimulating the survival of Th-17 effector cells or a cell that has initiated or is committed to the Th-17 developmental pathway; and/or v) stimulating the activity of effector Th-17 cells. In a specific embodiment, the methods of treatment comprise administering to a subject in need of such treatment a therapeutically effective amount of an agonist of Th-17 function that stimulates at least one of the commitment, development, maintenance, survival or activity of the Th-17 effector cell thereby increasing the Th-17 effector cell activity. Such antagonist may inhibit, directly or indirectly, the activity of an agent that inhibits the commitment, development, maintenance, survival or activity of the Th-17 effector cell, such as but not limited to, IFN-γ, IFN-α, IFN-β, IL-4 and/or IL-12. Such agonist may also stimulate, directly or indirectly the action of gene or polypeptide that is required or beneficial for the commitment, development, maintenance, survival or activity of the Th-17 effector cell or inhibit the action of a gene or polypeptide that is detrimental to the commitment, development, maintenance, survival or activity of the Th-17 effector cell. Furthermore, such agonist may stimulate, directly or indirectly, the commitment, development, maintenance, survival or activity of the Th-17 effector cell.

The method of prevention comprises the steps of identifying a subject in need of such prevention and initiating in said subject a treatment regimen that increases Th-17 function. In one embodiment, the method of prevention comprises i) stimulating the commitment to a Th-17 developmental pathway (such as by stimulating the commitment of a $CD4^+$ precursor cell, such as, but not limited to, naïve $CD4^+$ T cells); ii) stimulating the development of a precursor cell that has initiated or is committed to the Th-17 developmental pathway; iii) stimulating the maintenance of a Th-17 phenotype (i.e., the production of IL-17); iv) stimulating the survival of Th-17 effector cells or a cell that has initiated or is committed to the Th-17 developmental pathway; and/or v) stimulating the activity of effector Th-17 cells. In a specific embodiment, the methods of prevention comprise administering to a subject in need of such treatment a therapeutically effective amount of an agonist of Th-17 function that stimulates at least one of the commitment, development, maintenance, survival or activity of the Th-17 effector cell thereby increasing the Th-17 effector cell activity. Such antagonist may inhibit, directly or indirectly, the activity of an agent that inhibits the commitment, development, maintenance, survival or activity of the Th-17 effector cell, such as but not limited to, IFN-γ, IFN-α, IFN-β, IL-4 and/or IL-12. Such agonist may also stimulate, directly or indirectly the action of gene or polypeptide that is required or beneficial for the commitment, development, maintenance, survival or activity of the Th-17 effector cell or inhibit the action of a gene or polypeptide that is detrimental to the commitment, development, maintenance, survival or activity of the Th-17 effector cell. Furthermore, such agonist may stimulate, directly or indirectly, the commitment, development, maintenance, survival or activity of the Th-17 effector cell.

The antagonist for use in the methods of treatment and prevention may be a small molecule, a pharmaceutical, a specific antagonist of the signaling pathways for such stimulatory or inhibitory signals or for signaling pathways generated thereby, a non-coding RNA, an antisense nucleotide, an oligopeptide, or an antibody or portions thereof. Such antagonist may be provided as a pharmaceutical composition in a pharmaceutically acceptable carrier as described herein. In a specific embodiment, the antagonist is administered in a therapeutically effective amount. Such administration would thereby treat the disorder that is characterized, at least in part, by increased or aberrant Th-17 function. As discussed above, the treatment/prevention need not be absolute to provide benefit in the methods disclosed.

As discussed above, agonists of the Th-17 may be used in methods to treat and prevent disorders that are characterized, at least in part, by a decreased or aberrant Th-17 function. As such, agonists of Th-17 function are provided; such agonist may act by stimulating Th-17 commitment, development and/or activity. Such agonists encompass those that act by inhibiting, directly or indirectly, the signals that inhibit Th-17 commitment, development and/or activity, such as for example, by blocking inhibitory signals (for example, an anti-IL-4 antibody or an anti-IL-4R antibody). Such agonists also encompass those that act by providing, augmenting and/or stimulating, directly or indirectly, Th-17 commitment, development and/or activity, such as, for example, increasing commitment of $CD4^+$ precursor cells to Th-17 cells (such as for example, IL-6 or an agent that mimics the activity of IL-6). Such agonists further encompass those agents that stimulate, in whole or in part, the activity of genes and/or polypeptides specific to Th-17 function (those factors expressed in Th-17 cells, but not in or at reduced levels in Th-1, Th-2 or Th-1 and Th-2 cells). Examples of such proteins specific to Th-17 function are discussed herein (see Table 1 below). Factors that stimulate Th-17 function are discussed herein and known in the art and include, but are not limited to, TGF-β, IL-6, IL-17 and IL-23; factors that inhibit Th-17 function are discussed herein and known in the art and include, but are not limited to, IFN-γ, IFN-α, IFN-β, IL-4 and/or IL-12. Such agonists are useful, for example, for (i) treating and/or preventing disease states that are characterized, at least in part, by a decreased or aberrant Th-17 function; (ii) modulating the developmental pathway of Th-17 cells as described herein; and (iii) modulating the production of various cytokines and other signaling molecules produced by Th-17 cells or a cell that has initiated and/or is committed to the developmental pathway to produce a Th-17 cell.

In one embodiment, an agonist of Th-17 function is an antibody directed to a factor that inhibits Th-17 function or an antibody directed to a receptor for such factor. In one embodiment, the antibody is a blocking antibody that fully or partially blocks the interaction of the given factor with its receptor, whether the antibody is directed to the particular factor (for example, IL-4) or to a receptor for that factor (for example, the IL-4 receptor). In an alternate embodiment, the antibody is directed against the receptor for the factor and binds to the extracellular ligand binding domain of such receptor. Such antibody may block the activation of the receptor (as for an agent that inhibits Th-17 development, commitment and/or activity) or such antibody may stimulate the activity of such receptor (as for an agent that stimulates Th-17 commitment, development and/or activity).

In an alternate embodiment, an agonist of a Th-17 function is an oligopeptide that binds to a particular factor or a receptor for such factor. Such an oligopeptide may block the action of such factor, either by binding the factor itself of the receptor for such factor. In one embodiment, an oligopeptide binds to the extracellular ligand binding domain of the receptor. Oligopeptides may be chemically synthesized using known oligopeptide synthesis methodology or may be prepared and purified using recombinant technology. Such oligopeptides are usually at least about 5 amino acids in length, alternatively at least about 10, 25, 50, 75 or 100 amino acids in length. Such oligopeptides may be identified without undue experimentation using well known techniques. In this regard, it is noted that techniques for screening oligopeptide libraries for oligopeptides that are capable of specifically binding to a polypeptide target are well known in the art as described above. In certain embodiments, an oligopeptide may be conjugated to a cytotoxic agent or a diagnostic agent; such agents are well known in the art, as well as methods of conjugating such agents with oligopeptides.

In yet another alternate embodiment, an agonist of Th-17 function is an organic molecule that binds to a particular factor or a receptor for such factor (other than an oligopeptide or antibody as described above). In certain case, the organic molecule may block the activity of those agents that inhibit Th-17 function (as in the case of a compound that binds to IL-4 and prevents its interaction with the IL-4 receptor or a compound that binds to but does not activate or fully activate a receptor for a factor that is involved inhibiting Th-17 function); alternatively, the organic molecule may provide, augment or stimulate the activity of those agents that stimulate Th-17 function (as in the case of a compound that binds to the IL-6 receptor and stimulates, either in whole or in part the activity of such receptor). An organic molecule may be, for example, a pharmaceutical compound or an organic chemical compound. Such an organic molecule may be identified and chemically synthesized using known methodology (see, e.g., PCT Publication Nos. WO00/00823 and WO00/39585). Given the teachings of the prior art, such organic molecules may be identified without undue experimentation using well known techniques. In certain embodiments, an organic molecule may be conjugated to a cytotoxic agent or a diagnostic agent; such agents are well known in the art, as well as methods of conjugating such agents with oligopeptides.

In a further embodiment, an agonist of Th-17 function is a soluble form of the receptor, or portion thereof, for a specific factor (for example, a soluble form of the IFN-γ receptor that is not membrane bound that blocks IFN-γ activity; in some cases soluble antibody may also be stimulatory for such factor). Such soluble forms of the receptors may compete with membrane-bound forms of the receptor for binding to those factors that inhibit Th-17 function. The soluble form of the receptor may comprise all of the extracellular domain of the receptor or a ligand-binding portion of the extracellular domain of the receptor. In certain cases, the soluble form of the receptor may lack all or a portion of the transmembrane domain. The determination of the ligand-binding portion may be determined by methods that are well known in the art. Soluble forms of the receptors for Th-17 stimulating factors have been described (see, for example, WO/2005/039644, Biotherapy, Volume 11, Number 1/March, 1998 and Journal of Immunology, Vol 150, Issue 7 2698-2705 for a description of a soluble form of the IFN-γ receptor; U.S. Pat. No. 5,643,749 for a description of a soluble form of the IFN-α receptor; Hepatology, Volume 30, Issue 5, Pages 1325-1331 for a description of a soluble form of the IFN-B receptor; and 6063371 for a description of a soluble form of the IL-4 receptor).

In still a further embodiment, an agonist of Th-17 commitment, development and/or activity is a polynucleotide, such as, but not limited to, an antisense nucleic acid that decreases expression of a Th-17 inhibiting factor or a receptor for such factor. A decrease in expression may include a decrease in transcription of the gene and/or translation of the mRNA. An antisense nucleic acid may bind to a nucleic acid (DNA or RNA) encoding a Th-17 stimulating factor or a receptor for such factor. Such antisense nucleic acid may be an oligonucleotide of about 10-30 nucleotides in length. Such antisense oligonucleotide may comprise modified sugar-phosphodiester backbones or other sugar linkages, such as but not limited to phosphorothioate linkages and linkages as described in WO 91/06629. In a particular embodiment, the antisense nucleic acid is a short interfering RNA, a micro RNA, a short hairpin RNA or other RNA species that mediates RNA interference. The use of such techniques to regulate cytokine expression has been described (see US Publication Nos: 2005/0261219, 2005/0182007 and 2005/0143333). Also included are polynucleotides and other factors that increase the expression of factors that stimulate Th-17 function.

In yet a further embodiment, an agonist of Th-17 commitment, development and/or activity is an agent that itself directly or indirectly stimulates Th-17 commitment, development and/or activity. Exemplary agents are TGF-β, IL-6, IL-17 and/or IL-23. Furthermore, agonists also include agents that augment of mimic the activity of TGF-β, IL-6, IL-17 and/or IL-23 (such as an antibody that stimulates a receptor for TGF-β, IL-6, IL-17 and/or IL-23).

Furthermore, gene therapy method may be used to modulate Th-17 function and the pathways for Th-17 commitment, development and/or activity. Those cytokines and/or other molecules identified in stimulating or inhibiting Th-17 function or commitment, development and/or activity may be used with the teachings of this invention for gene therapy by introducing the desired gene for such cytokines and/or other molecules into the body of the patient. The desired gene may then be expressed and the treatment and/or prevention accomplished. As a result, such gene therapy methods may treat and prevent disease states and disorders that are characterized, at least in part, by decreased Th-17 function. Many methods exist for the introduction of genes or fragments thereof into a patient. For example, the gene may be introduced into a vector and introduced into the patient such that the gene or fragment thereof is expressed and the therapeutic potential realized. Exemplary methods of introduction include, but are not limited to, viral vectors (including retroviruses), naked nucleic acid and liposomes. Vectors may be introduced into a patient either in vivo or ex vivo. In the case of an in vivo treatment, the vector may be simply injected into the patient, for example parenterally, and allowed to find suitable target cells for gene expression. In the case of ex vivo treatment, cells are grown in vitro and transduced or transfected with the virus, embedded in a carrier such as a collagen matrix, which is then implanted in the patient, for example as a sub-cutaneous implant.

Methods of Identification

Furthermore, the teachings of the present disclosure can be used to identify compounds that activate or inhibit the Th-17 developmental pathway. The compounds identified may thus be useful in the treatment and/or prevention methods described above. Such compounds may be small molecule, pharmaceuticals, specific agonists or antagonist of the signaling pathways for such stimulatory or inhibitory signals, various non-coding RNAs, antisense molecules, polypeptides, antibodies, or specific compounds or portions thereof, that modulate Th-17 development The methods or assays for identifying such compounds comprise providing a cell line capable of development into a Th-17 effector cells, such as but not limited to CD4+ T cells and other cell types disclosed herein, incubating said cells with a candidate compound and measuring a response to said candidate compound. Such a response may be any response that is measurable using analytical techniques currently known in the art. Exemplary responses include, but are not limited to, an increase in cytokine expression, an increase in the level or activity of the polypeptides involved in Th-17 development, an increase in the level or activity of the polypeptides involved in Th1 or Th2 development. The results section of this disclosure provides exemplary endpoints for use in the disclosed methods and assays, as well as exemplary model systems, both in vitro and in viva for use in the disclosed methods and assays. Exemplary cytokines include, but are not limited to, IFN-γ, IL-12, IL-4, TGF-β, IL-23, IL-1, IL-17 and/or IL-6. In addition, the response to said candidate compound measured may be a decrease in any of the criteria discussed above.

Furthermore, the present disclosure provides methods for identifying the genes and polypeptides involved in Th-17 function. In one embodiment, those genes and polypeptides involved in the early stages of Th-17 commitment and development may be identified. The methods for such analysis and exemplary results are provided in the results section below. The methods described comprise providing a cell line that has matured into a Th-17 effector cell or providing a CD4+ precursor cell and stimulating the development of such precursor cell into a Th-17 effector cell. Total RNA is isolated from such cell and cDNA may be produced. The cDNA may be analyzed by methods known in the art, such as, but not limited to, using DNA microarray technology. The process can be repeated for other cell types as well; for example, undifferentiated CD4+ naïve T cells, Th1 and/or Th-2 cells may be used. A comparison made between the cell types to determine which genes and/or proteins are expressed in Th-17 cells or cells that are committed to Th-17 development.

As would be obvious to one of ordinary skill in the art, when a precursor cell is stimulated to develop into a Th-17 effector cell, the gene identification analysis can be carried out at various stages of Th-17 development (such as for example, immediately after TGF-β and/or IL-6 exposure, but prior to exposure to IL-23).

Methods of Obtaining a Th-17 Effector Cell

The present disclosure also describes a purified Th-17 effector cell. Such a Th-17 effector cells was not previously appreciated in the art. Methods for generating such Th-17 effector cells are described.

The present disclosure also discloses methods for generating a Th-17 effector cells, both in vivo and in vitro. In one embodiment, the method comprising the steps of exposing a Th-17 effector cell precursor cell to a Th-17 agonist that stimulates Th-17 effector cell commitment, development, maintenance, survival and/or activity.

The present disclosure also discloses methods for inhibiting the generation of a Th-17 effector cells, both in vivo and in vitro. In one embodiment, the method comprising the steps of exposing a Th-17 effector cell precursor cell to a Th-17 antagonist that inhibits Th-17 effector cell commitment, development, maintenance, survival and/or activity.

Agonists and antagonist of Th-17 are described as above, along with the factors that stimulate and inhibit Th-17 effector cell commitment, development, maintenance, survival and/or activity.

Pharmaceutical Compositions

The compounds described in the present disclosure described above for use in the methods described herein may be administered alone or as a pharmaceutical composition formulated by any method known in the art. Certain exemplary methods for preparing the compounds and pharmaceutical compositions are described herein and should not be considered as limiting examples. Furthermore, the compounds or pharmaceutical compositions may be administered to the subject as is known in the art and determined by a healthcare provider. Certain modes of administration are provided herein and should not be considered as limiting examples. Furthermore, the compound or pharmaceutical composition may be administered with other agents in the methods described herein. Such other agents may be agents that increase the activity of the compounds disclosed, such as by limiting the degradation or inactivation of the compounds disclosed or increasing the absorption or activity of the compounds disclosed.

The compounds and pharmaceutical compositions described can be used in the form of a medicinal preparation, for example, in aerosol, solid, semi-solid or liquid form which contains the compounds disclosed as an active ingredient. In addition, the pharmaceutical compositions may be used in an admixture with an appropriate pharmaceutically acceptable carrier. Such pharmaceutically acceptable carriers include, but are not limited to, organic or inorganic carriers, excipients or diluents suitable for pharmaceutical applications. The active ingredient may be compounded, for example, with the usual non-toxic pharmaceutically acceptable carriers, excipients or diluents for tablets, pellets, capsules, inhalants, suppositories, solutions, emulsions, suspensions, aerosols and any other form suitable for use. Pharmaceutically acceptable carriers for use in pharmaceutical compositions are well known in the pharmaceutical field, and are described, for example, in Remington: The Science and Practice of Pharmacy Pharmaceutical Sciences, Lippincott Williams and Wilkins (A. R. Gennaro editor, 20$^{th}$ edition). Such materials are nontoxic to the recipients at the dosages and concentrations employed and include, but are not limited to, water, talc, gum acacia, gelatin, magnesium trisilicate, keratin, colloidal silica, urea, buffers such as phosphate, citrate, acetate and other organic acid salts, antioxidants such as ascorbic acid, low molecular weight (less than about ten residues) peptides such as polyarginine, proteins, such as serum albumin, gelatin, or immunoglobulins, hydrophilic polymers such as polyvinylpyrrolidinone, amino acids such as glycine, glutamic acid, aspartic acid, or arginine, monosaccharides, disaccharides, and other carbohydrates including cellulose or its derivatives, lactose, mannitol, glucose, mannose, dextrins, potato or corn starch or starch paste, chelating agents such as EDTA, sugar alcohols such as mannitol or sorbitol, counterions such as sodium and/or nonionic surfactants such as Tween, Pluronics or polyethyleneglycol. In addition, the pharmaceutical compositions may comprise auxiliary agents, such as, but not limited to, taste-enhancing agents, stabilizing agents, thickening agents, coloring agents and perfumes.

Pharmaceutical compositions may be prepared for storage or administration by mixing a compound of the present disclosure having a desired degree of purity with physiologically acceptable carriers, excipients, stabilizers, auxiliary agents etc. as is known in the pharmaceutical field. Such pharmaceutical compositions may be provided in sustained release or timed release formulations.

The pharmaceutical compositions may be administered orally in solid dosage forms, such as capsules, tablets, and powders, or in liquid dosage forms, such as elixirs, syrups and suspensions. It can also be administered parenterally, in sterile liquid dosage forms. Furthermore, pharmaceutical compositions may be administered parenterally by transmucosal delivery via solid, liquid or aerosol forms of transdermally via a patch mechanism or ointment. Various types of transmucosal administration include respiratory tract mucosal administration, nasal mucosal administration, oral transmucosal (such as sublingual and buccal) administration and rectal transmucosal administration.

For preparing solid compositions such as, but not limited to, tablets or capsules, the pharmaceutical compositions may be mixed with an appropriate pharmaceutically acceptable carriers, such as conventional tableting ingredients (lactose, sucrose, mannitol, corn starch, potato starch, alginic acid, microcrystalline cellulose, acacia, gelatin, gums, colloidal silicon dioxide, croscarmellose sodium, talc, sorbitol, stearic acid magnesium stearate, calcium stearate, zinc stearate, stearic acid, dicalcium phosphate other excipients, colorants, diluents, buffering agents, disintegrating agents, moistening agents, preservatives, flavoring agents, and pharmacologically compatible carriers) and diluents (including, but not limited to, water, saline or buffering solutions) to form a substantially homogenous composition. The substantially homogenous composition means the components (a compound as described herein and a pharmaceutically acceptable carrier) are dispersed evenly throughout the composition so that the composition may be readily subdivided into equally effective unit dosage forms such as tablets, pills and capsules. The solid compositions described may be coated or otherwise compounded to provide a dosage form affording the advantage of prolonged action. For example, the tablet or pill can comprise an inner dosage an outer dosage component, the latter being in the form of an envelope over the former. The two components can be separated by an enteric layer which serves to resist disintegration in the stomach and permits the inner component to pass intact through the stomach or to be delayed in release. A variety of materials can be used for such enteric layers or coatings such materials including a number of polymeric acids and mixtures of polymeric acids with such materials as shellac, cetyl alcohol and cellulose acetate. The active compounds may also be formulated in rectal compositions such as suppositories or retention enemas, e.g., containing conventional suppository bases such as cocoa butter or other glycerides. The solid compositions may also comprise a capsule, such as hard- or soft-shelled gelatin type containing, for example, surfactants, lubricants, and inert fillers, such as lactose, sucrose, calcium phosphate, and corn starch.

For intranasal administration, intrapulmonary administration or administration by other modes of inhalation, the pharmaceutical compositions may be delivered in the form of a solution or suspension from a pump spray container or as an aerosol spray presentation from a pressurized container or nebulizer, with the use of a suitable propellant (e.g., dichlorodifluoromethane, trichlorofluoromethane, dichlorotetrafluoroethane, nitrogen, propane, carbon dioxide or other suitable gas) or as a dry powder. In the case of an aerosol or dry powder format, the amount (dose) of the compound delivered may be determined by providing a valve to deliver a metered amount.

Liquid forms may be administered orally, parenterally or via transmucosal administration. Suitable forms for liquid administration include aqueous solutions, suitably flavored syrups, aqueous or oil suspensions, and flavored emulsions with edible oils such as cottonseed oil, sesame oil, coconut oil, or peanut oil as well as elixirs and similar pharmaceutical vehicles. Suitable dispersing or suspending agents for aqueous suspensions include synthetic natural gums, such as tragacanth, acacia, alginate, dextran, sodium carboxymethyl cellulose, methylcellulose, polyvinylpyrrolidone or gelatin. Such liquid preparations may be prepared by conventional means with pharmaceutically acceptable additives such as suspending agents (e.g., sorbitol syrup, methyl cellulose or hydrogenated edible fats); emulsifying agents (e.g., lecithin or acacia); non-aqueous vehicles (e.g., almond oil, oily esters or ethyl alcohol); preservatives (e.g., methyl or propyl p-hydroxybenzoates or sorbic acid); and artificial or natural colors and/or sweeteners. Liquid formulations may include diluents, such as water and alcohols, for example, ethanol, benzyl alcohol, propylene glycol, glycerin, and the polyethylene alcohols, either with or without the addition of a pharmaceutically acceptable surfactant, suspending agent, or emulsifying agent. For buccal or sublingual administration, the composition may take the form of tablets or lozenges formulated in conventional manners. Lozenge forms can comprise the active ingredient in a flavor, usually sucrose and acacia or tragacanth, as well as pastilles comprising the active ingredient in an inert base, such as gelatin and glycerin, or sucrose and acadia, emulsions, and gels containing, in addition to the active ingredient, such carriers as are known in the art.

The compounds disclosed (whether alone or in pharmaceutical compositions) may be formulated for parenteral administration. Parenteral administration includes, but is not limited to, intravenous administration, subcutaneous administration, intramuscular administration, intradermal administration, intrathecal administration, intraarticular administration, intracardiac administration, retrobulbar administration and administration via implants, such as sustained release implants.

The pharmaceutical compositions may be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets. The requirements for effective pharmaceutically acceptable carriers for injectable compositions are well known to those of ordinary skill in the art. See Pharmaceutics and Pharmacy Practice, J.B. Lippincott Co., Philadelphia, Pa., Banker and Chalmers, Eds., 238-250 (1982) and ASHP Handbook on Injectable Drugs, Toissel, 4th ed., 622-630 (1986).

The pharmaceutical compositions are administered in therapeutically effective amount. The therapeutically effective amount will, of course, vary depending upon known factors, such as the pharmacodynamic characteristics of the particular compound and its mode and route of administration; the age, health and weight of the subject; the severity and stage of the disease state or condition; the kind of concurrent treatment; the frequency of treatment; and the effect desired. The total amount of the compound administered will also be determined by the route, timing and frequency of administration as well as the existence, nature, and extent of any adverse side effects that might accompany the administration of the compound and the desired physiological effect. It will be appreciated by one skilled in the art that various conditions or diseases, in particular chronic conditions or diseases, may require prolonged treatment involving multiple administrations.

Results

In the following results, the methods used were those methods specified in the Methods section of the present disclosure and the references cited therein.

Th1 and Th2 Cells Respond Poorly to IL-23

IL-23 acts mainly on effector and/or memory $CD4^+$ T cells to induce proliferation and IL-17 secretion (5,18) This is ascribed to expression of IL-23 receptor (IL-23R) by effector and/or memory cells, particularly Th1 cells, but not by naive T cells. However, the effects of IL-23 on defined populations of Th1 and Th2 cells have not been reported. In order to examiner the effects of IL-23 stimulation in vitro, naive CD4+ T cells were differentiated under Th1- or Th2-polarizing conditions, then assessed their responsiveness to IL-23 as measured by cell proliferation (FIG. 1a) and cytokine production (FIG. 1b).

In FIG. 1a, CD4+ T cells were activated in Th1- or Th2-polarizing conditions for 5 days as described in the methods section and assessed for their ability to proliferate. B6 Th1 and Th2 CD4+ T cells were cultured for 3 days with IL-2 of Il-2 plus 1 ng/ml or 10 ng/ml IL-23 with or without anti-CD3 antibody. Proliferation was assessed by the addition of $^3$H-thymidine during the final 24 hours. Error bars represent=standard deviation with breaks in the bars indicating a change of scale. The addition of IL-23 did not significantly enhance the proliferation of either Th1 or Th2 cells compared with that of control, IL-2 treated cells, whether re-stimulated in the presence or absence of antibody to CD3 (anti-CD3; P<0.05) (FIG. 1a).

In FIG. 1b, Th1 and Th2 cells were grown under Th1- and Th2-polarizing conditions as in FIG. 1a and re-stimulated with anti-CD3 and IL-2 or IL-2 plus IL-23. After 5 days of re-stimulation, intracellular cytokine staining for IFN-γ and IL-17 (Th1 cells, left) or IL-4 and IL-17 (Th2 cells, right) was accomplished 5 hours after activation with PMA and ionomycin. Plots are gated on CD4+ T cells with number in the quadrants indicating the frequency of cells staining positive for the cytokines along the arrows. The data are representative of two independent experiments. Consistent with the results of FIG. 1a, re-stimulation of Th1 and Th2 populations with IL-23 induced no appreciable Increase in IL-17 positive cells compared with that of the control (FIG. 1b). The results were confirmed by real time PCR (data not shown). These data show that IL-23 has limited effects on Th1- and Th2-polarized effector T cells.

INF-γ Inhibits the Development of Th-17 Cells

Figure 2:
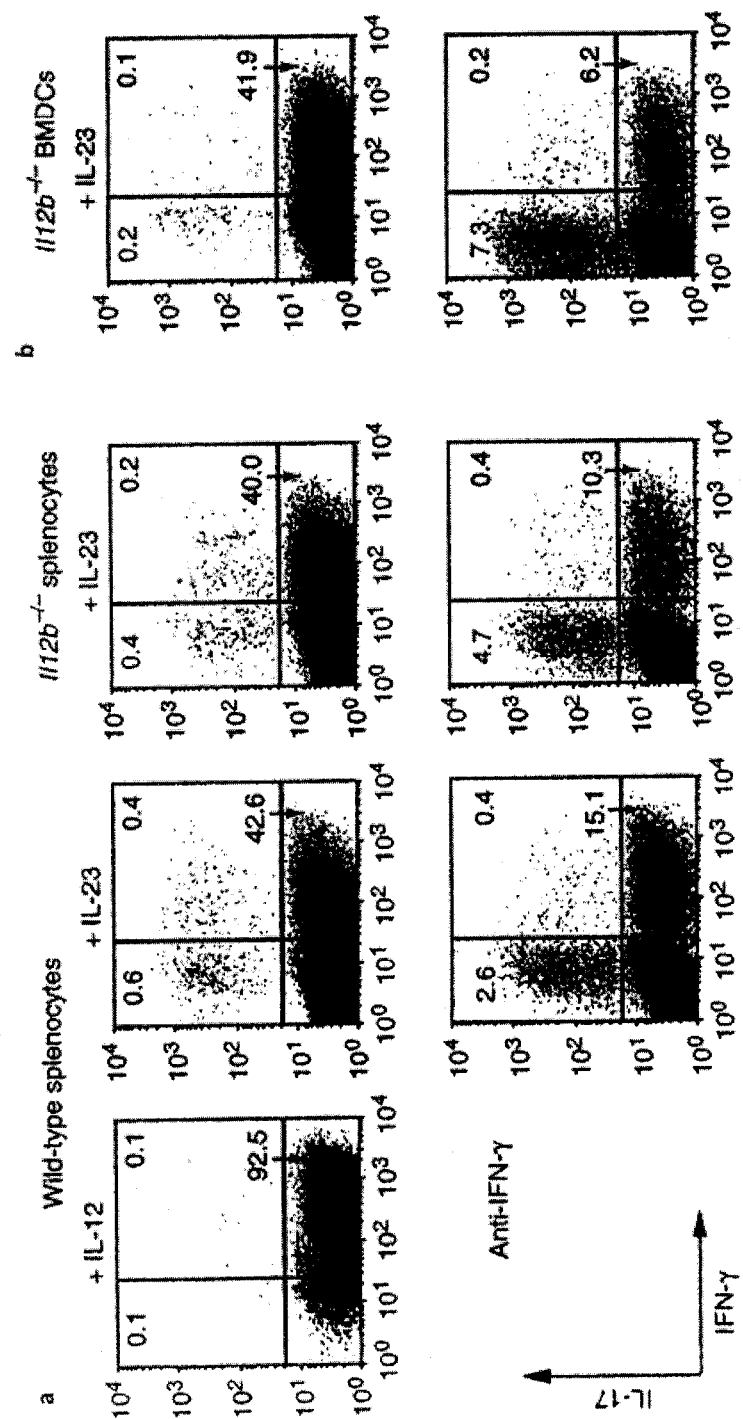
FIG. 2 illustrates that IFN-$\gamma$ inhibits the development of IL-17 producing effector cells (Th-17 cells) as measured by IL-17 producing cells.

The limited effects of IL-23 on Th1 and Th2 cells suggested that IL-23 might be acting on a distinct CD4+ effector T cell subpopulation or perhaps before Th1 and Th2 commitment. To examine this, freshly isolated CD4+ T cells were activated in Th2-neutralizing conditions (with anti-IL-4) and the effects of IL-12 and IL-23 on the development of IL-17-producing T cells was determined. CD4+ T cells from B6 mice were isolated and stimulated with splenocytes or mature BMDCs as well as exogenous cytokines to induce effector T cell differentiation. In FIG. 2a, shows flow cytometric analysis of B6 CD4+ T cells activated with anti-CD3 in the presence of B6 (wild-type) or IL-12p40 deficient (Il12b −/−) splenocytes. Cells were cultured with IL-12, IL-23 or IL-23 plus IFN-g. After 5 days, CD4+ T cells were re-stimulated for 5 hours with PMA and ionomycin and subject to FACS analysis. Plots are gated on CD4+ T cells with number in the quadrants indicating the frequency of cells staining positive for the cytokines along the arrows. The data are representative of two to three independent experiments.

As shown in FIG. 2a, the majority of CD4+ T cells cultured with IL-12 in IL-4 neutralizing conditions produced IFN-g and there was no substantial development of Th-17 cells. Unexpectedly, a considerable fraction (about 40%) of CD4+ T cells activated with IL-23 in IL-4-neutralizing conditions also produced IFN-g, and only a small fraction (about 1%) of CD4+ T cells produced IL-17. Because the receptors for IL-12 and IL-23 share the common IL-12Rβ1 chain, the experiment shown in FIG. 2a was repeated in IL-12-deficient conditions to eliminate the possibility that IL-12 might be interfering with IL-23 signaling. CD4+ T cells were activated in IL-4-neutralizing conditions using IL-12p40-deficient splenocytes, which lack both IL-12 and IL-23, with added IL-23. In these conditions, the fractions of effector T cells that produced IFN-γ and IL-17 were comparable to those noted with IL-12-competent, wild-type splenocytes, with only a very small frequency of T cells producing IL-17. Thus, even in the absence of IL-12, IL-23 failed to enhance the development of Th-17 cells from precursor cells, showing that the lack of IL-17 induction was not tied to inhibitory actions of IL-12.

It was notable that IL-23 supplementation of CD4+ T cell cultures resulted in a large population of IFN-γ-expressing, Th1-like CD4+ T cells, even in the absence of IL-12 signaling. This was not due to enhanced expression of IFN-γ by IL-23, because there was a comparable frequency of IFN-γ+ CD4+ T cells after activation without the addition of exogenous IL-23. It was possible that IFN-γ, not IL-12, in these cultures might be promoting Th1 cell development and preventing the generation of IL-17-producing CD4+ cells. To examine this possibility, IFN-γ was neutralized in concert with IL-23 supplementation. The activation of freshly isolated CD4+ T cells with IL-23 and anti-IFN-γ led to the development of a discrete subpopulation of IL-17+ T cells and 'dampened' the development of IFN-γ cells. As shown in FIG. 2a, treatment with IL-23 and anti-IFN-γ resulted in 3.0% or 5.1% of CD4+ T cells produced IL-17 when differentiated in the presence of wild-type or IL-12p40-deficient splenocytes, respectively. This occurred regardless of the capacity of splenocytes to produce IL-12.

Because of the heterogeneous nature of the antigen-presenting cell (APC) population used in the experiments described above and shown in FIG. 2a, the findings were confirmed using a defined population of APCs. Mature bone marrow-derived dendritic cells (BMDCs) from IL-12p40-deficient mice were differentiated and used as APCs to activate CD4+ T cells with or without IFN-γ neutralization. In FIG. 2b, B6 CD4+ T cells were activated with anti-CD3 and IL-23 with or without IFN-γ and mature bone marrow-derived dendritic cells (BMDCs) from IL-12p40-deficient (Il12b −/−) mice. In parallel to results obtained with IL-12p40-deficient splenocytes as APCs, IL-23 alone did not induce a prominent fraction of IL-17+ T cells unless endogenous IFN-γ was neutralized. These data collectively establish that IFN-γ but not IL-12 inhibits the development of Th-17 effector cells. Notably, the expression of IL-17 and IFN-γ by individual T cells demonstrated a strong tendency toward mutual exclusion.

Development of Th-17 Cells from Naïve Precursor Cells

It has been reported that the effects of IL-23 are limited mainly to effector and memory CD4+ T cells, with minimal or no action on naïve CD4+ T cells (Aggarwal, J. Biol. Chem., 278:1910 (2003); Oppmann, Immunity, 13:715 (2000)). However, data above suggested that IL-23 might promote the development of IL-17-producing effector cells from naive precursor cells. Although in the experiments reported above CD4+ T cells were purified from un-manipulated mice, the possibility that the starting T cell populations were contaminated with a minor fraction of effector and/or memory cells from which IL-17 producers developed could not be excluded. To address this issue, the studies using naive CD4+ T cells were repeated using naïve CD4+ T cells isolated from DO11.RAG TCR-transgenic mice deficient in recombination-activating gene 2 (DO11.RAG mice). These experiments also provided a system for studying the generation of Th-17 cells using an antigen specific model. DO11.RAG mice T cells were activated with ovalbumin (OVA) peptide and IL-12 or IL-23, with or without IFN-γ neutralization.

Figure 3:
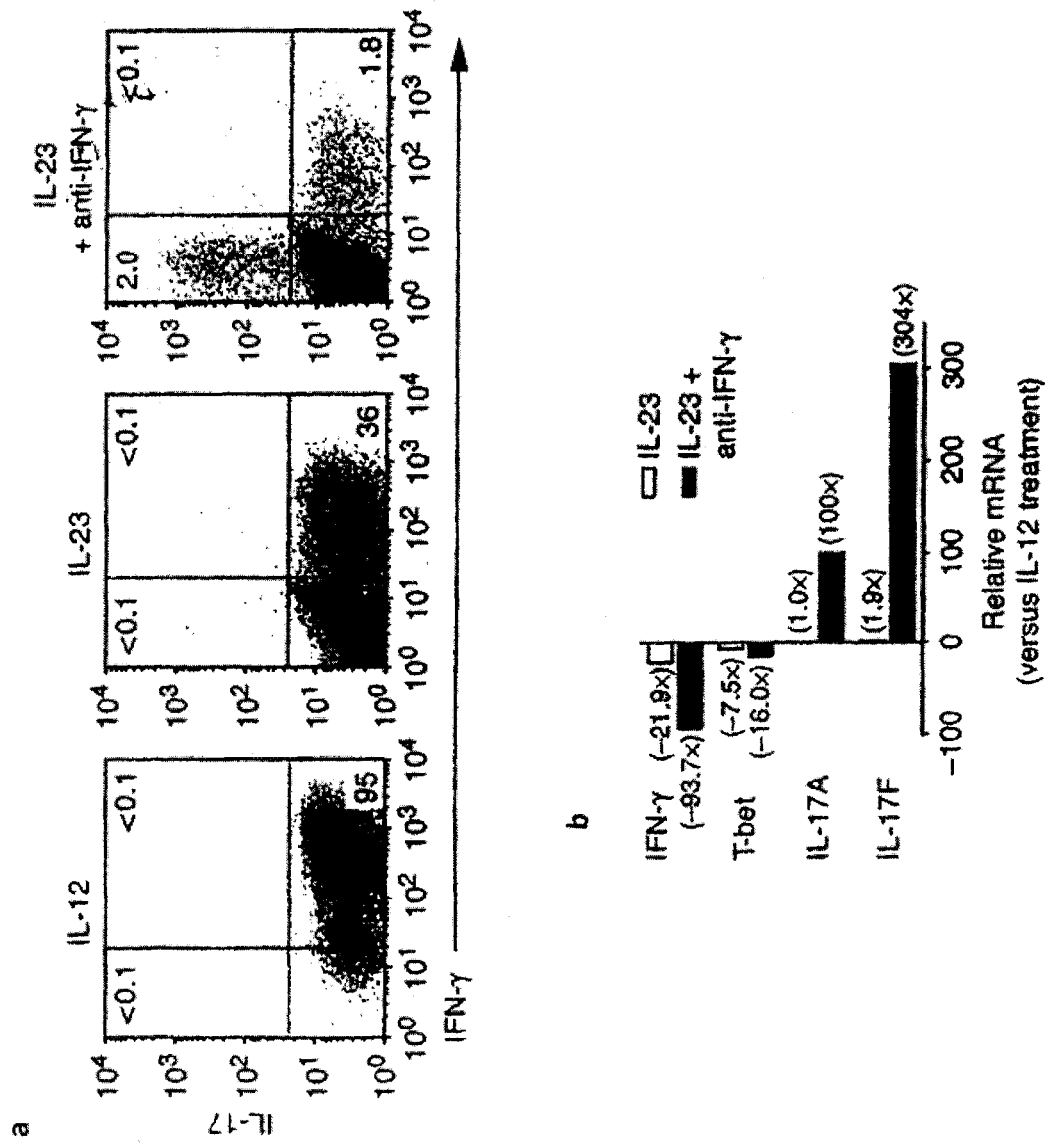
FIG. 3 shows the differentiation of IL-17 producing effector cells (Th-17 cells) from naïve CD4+ T cells.

In FIG. 3a, T cells from DO11.RAG mice were stimulated with OVA peptide-pulsed BALB/c splenic feeder cells and IL-12, IL-23 or IL-23 with anti-IFN-γ. After 5 days incubation, cytokine expression at the single-cell level was measured by FACS after re-stimulation with PMA and ionomycin for 5 hours. As expected, activation of DO11.RAG T cells in the presence of IL-12 induced the development of a strongly polarized Th1 phenotype with no detectable IL-17-producing cells (FIG. 3a). In the presence of exogenous IL-23, a reduced yet considerable fraction of IFN-γ-producing effector cells developed (about 35%), again in the absence of detectable IL-17-producing cells. In contrast, activation of DO11.RAG T cells with IL-23 and neutralizing anti-IFN-γ resulted in the development of a distinct IL-17+ IFN-γ negative effector T cell population, with a substantial reduction of IFN-γ-producing cells (FIG. 3a).

To confirm and extend those results, the IL-23-dependent expression of a second IL-17 family member, IL-17F which is tightly linked with IL-17 (or IL-17A) on mouse chromosome 1 and may be coordinately expressed with IL-17 (ref 25) was examined. The expression of IL-17F using real-time PCR was determined and compared with the expression IFN-γ IL-17 and T-bet for each of the polarized T cell populations. In FIG. 3b, the relative mRNA levels were compared versus IL-12 treatment with actual values for difference given in parentheses. In comparison with IL-12-polarized Th1 cells, IL-23-stimulated naive DO11 RAG T cells expressed 22× less IFN-γ mRNA, 2× more IL-17F mRNA, and the same amount of IL-17 mRNA. In contrast and in agreement with the intracellular cytokine data, DO11.RAG T cells activated with IL-23 in the presence of anti-IFN-γ showed a 94× decrease in IFN-γ mRNA but a substantial up-regulation of both IL-17 and IL-17F mRNA (increases of 100× and 301×, respectively). Notably, T-bet mRNA expression was substantially reduced in both conditions, including IL-23 stimulation. IL-23-stimulated CD4+ T cells demonstrated an 8× decrease in T-bet mRNA compared with that of IL-12-polarized Th1 cells, whereas cultures in which IFN-γ was blocked showed a 16× decrease in T-bet mRNA (FIG. 3b). These data parallel the single-cell expression analyses above and establish the idea that in absence of IFN-γ signaling, naive CD4+ T cell precursor cells activated in the presence of IL-23 develop into Th-17 effector cells that coordinately express IL-17A and IL-17F.

Type I and Type II Interferons Inhibit Th-17 Development

Figure 4:
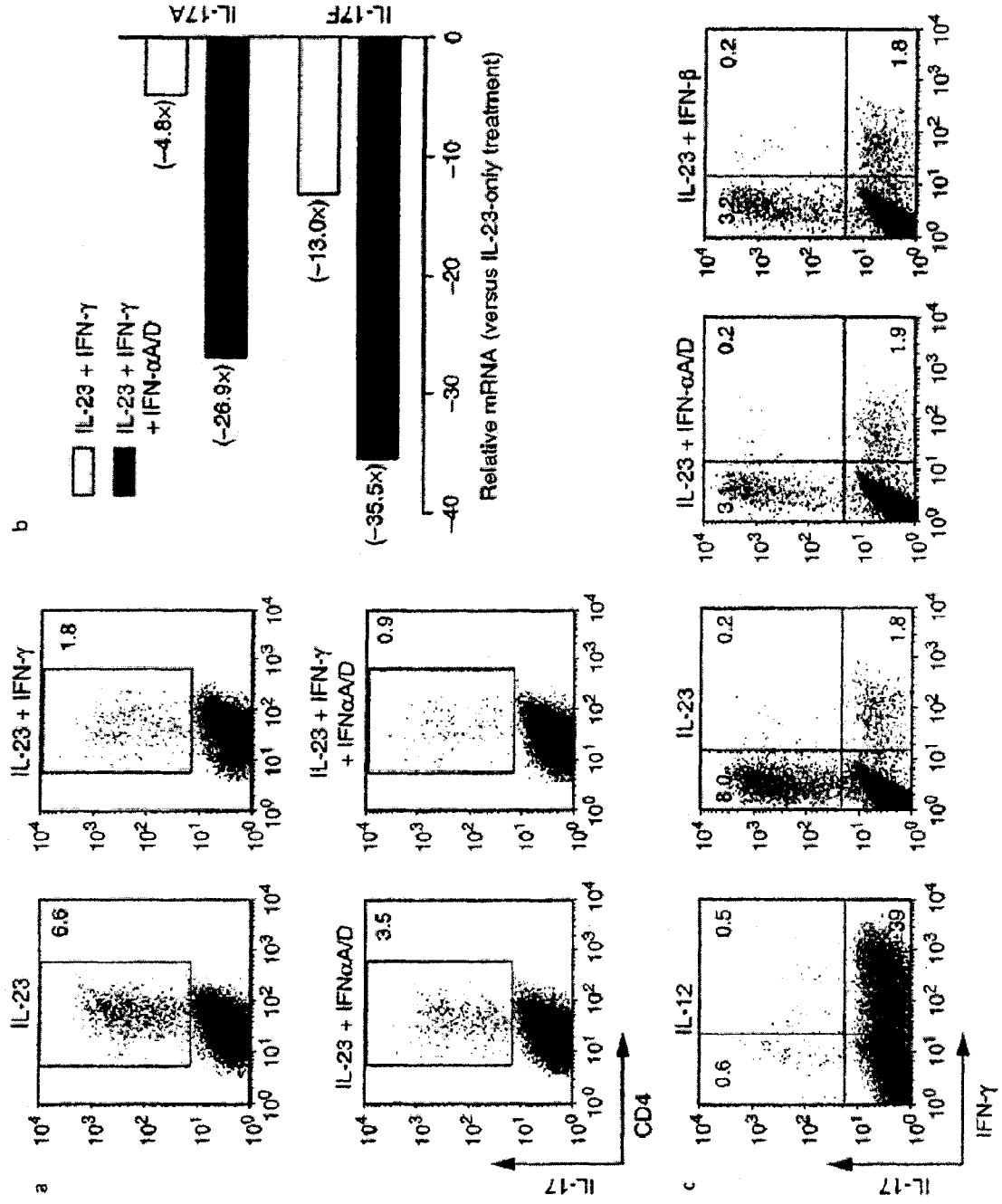
FIG. 4 illustrates that both type I and type II interferons inhibit the development of IL-17 producing effector cells (Th-17 cells).

In the experiments above, the development of IL-17 effector cells was elicited most prominently by the addition of IL-23 to cultures with limited IFN-γ production or neutralization of IFN-γ. To confirm and extend those observations, two systems devoid of IFN-γ production or signaling were employed: IFN-γ deficiency and IFN-γ R deficiency, respectively[26,27]. In agreement with results of the IFN-γ neutralization experiments (FIG. 2), cultures in which both the APCs and CD4+ T cells were prepared from IFN-γ-deficient mice demonstrated enhanced production of IL-17. In FIG. 4a, IFN-γ-deficient CD4+ T cells were activated with IFN-γ-deficient splenocytes, anti-CD-3 and IL-23. Cultures were also treated with IFN-γ, IFN-αA/D or IFN-γ plus IFN-αA/D. After 5 days in culture, CD4+ T cells were collected and re-stimulated with PMA and ionomycin for 5 hours before intracellular staining for IL-17. As can be seen in FIG. 4a the addition of exogenous IFN-γ substantially inhibited the development of IL-17 producing effector cells from IFN-γ-deficient precursor cells, establishing the idea of a direct function for IFN-γ in the blockade of Th-17 cell development. The results were confirmed by determining IL-17A and IL-17F mRNA expression by real-time PCR where the number in parentheses denotes fold-reduction (FIG. 4b). Similar results were obtained in experiments with IFN-γR-deficient cells (FIG. 4c). In FIG. 4c, IFN-γR-deficient CD4+ T cells were activated with IFN-γR-deficient splenocytes, anti-CD-3, IL-12 and IL-23. Cultures were also treated with IFN-β or IFNαA/D. After 5 days in culture, CD4+ T cells were collected and re-stimulated with PMA and ionomycin for 5 hours before intracellular staining for IL-17 and IFN-γ. Plots for FIGS. 4a and 4c are gated on CD4+ T cells with the numbers in the quadrants indicative of the percent of CD4+ T cells staining positive for the cytokine along the axis. Data are representative of 3-4 experiments.

Although IFN-γ is an important proximal cytokine in the initiation of Th1 cell development, other cytokines that share with IFN-γ the ability to recruit STAT1 signaling, such as type I interferons, can contribute. Therefore, the possible inhibitory effects type I interferons on Th-17 effector development were examined. As described above, these experiments were conducted under conditions in which IFN-γ signaling was absent IFN-γ-deficient CD4+ T cells were activated with anti-CD3 and IL-23 with the addition of IFN-αA/D and assessed IL-17 effector development (FIGS. 4a and b). The presence of type I interferon inhibited Th-17 cell development, as indicated by a reduced frequency of IL-17+ CD4+ T cells, albeit not to the extent noted for IFN-γ (FIG. 4a). An analogous series of experiments using IFN-γR-deficient CD4+ T cells yielded similar results; both IFN-αA/D and IFN-β reduced the frequency of IL-17+ CD4+ T cells (FIG. 4c). Moreover, when IL-23-activated IFN-γ-deficient CD4+ T cells were supplement with both IFN-γ and IFN-αA/D, there was additive inhibition of IL-17 production (FIGS. 4a and b). These data suggest that type 1 and type II interferons and possibly other STAT1 activating ligands can inhibit the development of Th-17 effector cells.

Th-17 Development does not Require STAT1 or T-Bet

Figure 5:
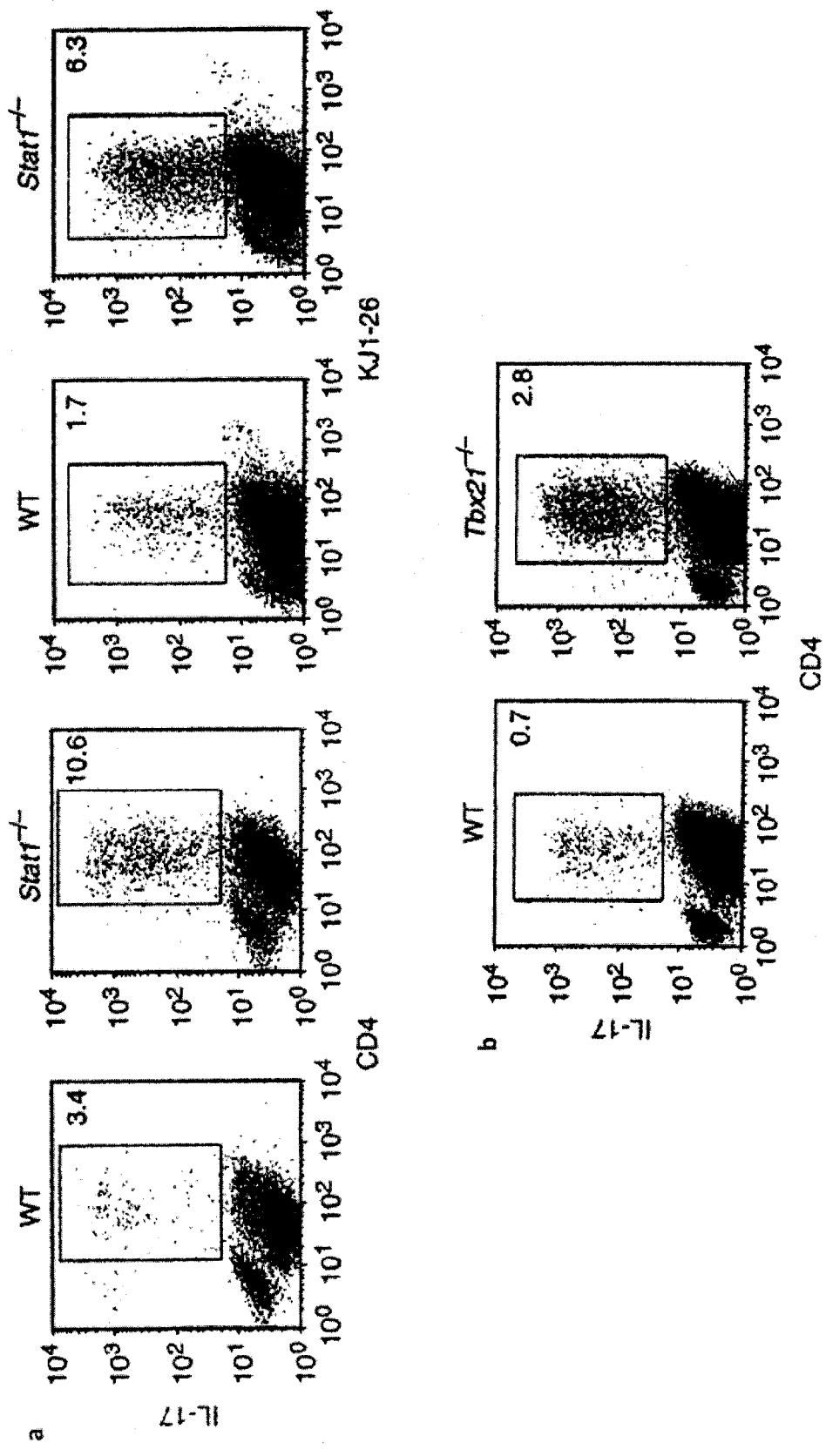
FIG. 5 shows the development of IL-17 producing effector cells (Th-17 cells) is independent of the Th1-associated signaling molecules STAT1 and T-bet.

The initiation of Th1 cell differentiation requires STAT1 signaling, which can be recruited by IFN-γ, as well as type I interferons and IL-27. The inhibitory actions of type I and II interferons on the development of the IL-17 phenotype suggested a possible inverse association between STAT1 signaling and the development of IL-17 effector cells. To explore this, IL-17 effector cell development of wild-type and STAT1-deficient T cells was compared in the presence of exogenous IL-23 and anti-IL-4. In FIG. 5a, 136 (left panels) and DO11.10 TCR-transgenic (right panel) wild-type (WT) and Stat1 −/− CD4+ T cells were collected and activated with an appropriate splenic feeder cell population, IL-23 and anti-CD3 or OVA peptide, respectively. After 5 days incubation, intracellular cytokine staining for IL-17 was accomplished after 5 hours activation with PMA and ionomycin. The numbers beside the gated cell population indicated the percent CD4+ or KJI-26+CF4+ T cells staining positive for IL-17. In the absence of STAT1, Th-17 cell development proceeded without a requirement for IFN-γ neutralization (FIG. 5a), establishing an important function for STAT1 in the suppression of Th-17 cell differentiation.

STAT1 signaling induces expression of T-bet, which is critical for Th1 cell development through its actions promoting IL-12Rβ2 expression, among other potential effects[23,33]. In the absence T-bet, IFN-γ production by CD4+ T cells is impaired even in the presence of exogenous IL-12 (ref. 33). Because it has been suggested that IL-23 acts on cells of the Th1 lineage to induce proliferation and IL-17 secretion, experiments were performed to determine whether T-bet expression is required for the development of IL-17 effector cells. Given the reduced expression of T-bet noted in DO11.RAG CD4+ T cells activated with IL-23 (FIG. 3b) and the demonstration of STAT1-independent development of IL-17 effector cells (FIG. 5a), however, it was also possible that T-bet was not required for IL-17 effector cell development and might be inhibitory to such development. In FIG. 5b, wild-type (WT) and T-bet-deficient (Tbx21−/−) CD4+ T cells were collected and activated with BALB/c splenic feeder cells, anti-CD3 and IL-23 in IL-4 neutralizing conditions. After 5 days incubation, cells were analyzed for IL-17 staining as in FIG. 5a. Even in the absence of treatment with anti-IFN-γ, T-bet-deficient T cells demonstrated augmented development of IL-17 effector cells, indicating that this transcription factor is dispensable for IL-17 production by CD4+ T cells and could be an important mediator of IFN-γ-associated blockade of Th-17 cell development. Along with the data establishing a negative association between Th1-associated interferon-STAT1 signaling pathway and Th-17 cell development, these data support a model in which expression of the gene encoding IL-17 is linked to a distinct effector lineage. Such information was not previously appreciated in the art.

INF-γ Inhibits Expression of IL-23R

Figure 6:
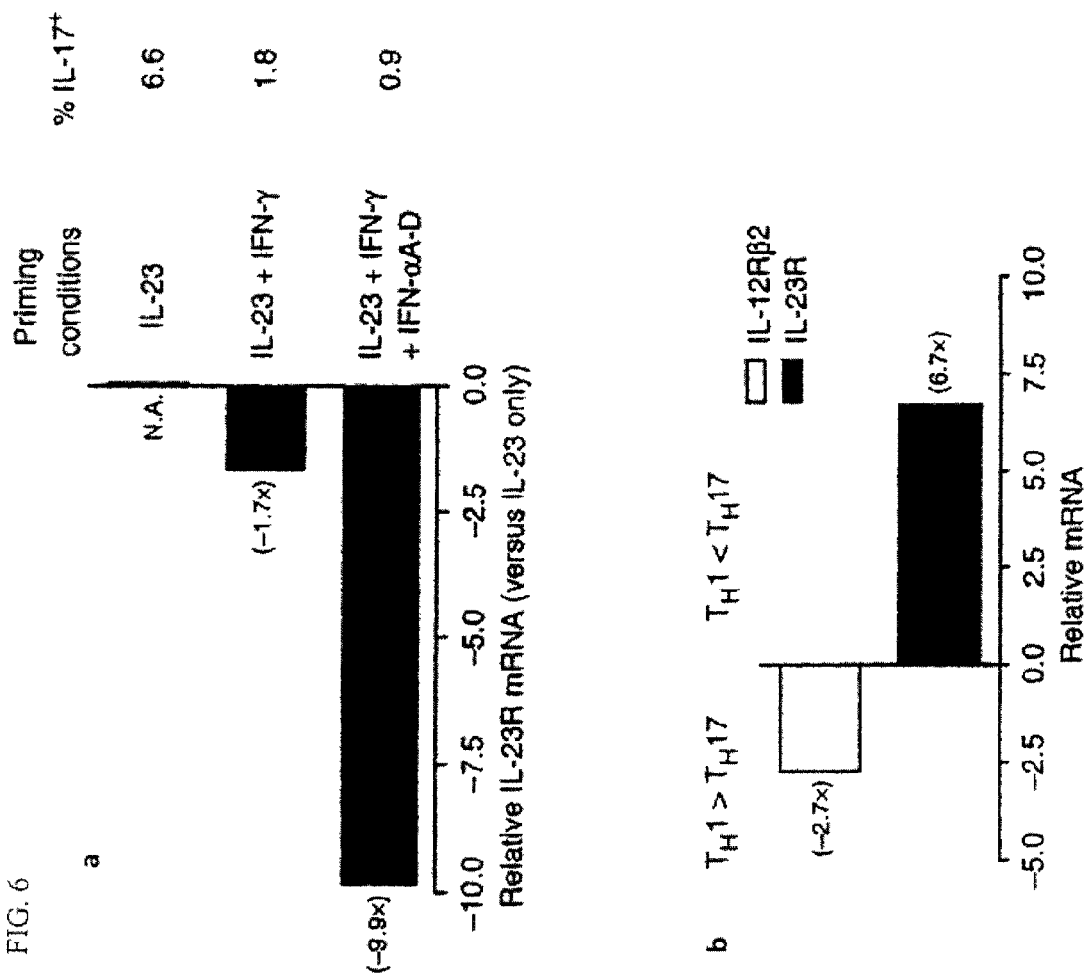
FIG. 6 shows the differential expression of IL-12R (Th1 associated) and IL-23R (Th-17 associated) by Th1- and Th-17-polarized effector cell populations.

Commitment to the Th1 lineage is associated with STAT1-induced expression of the IL-12Rβ2 chain of the IL-12R complex via T-bet. Because deficiencies STAT1 and T-bet did not preclude IL-23-induced development of Th-17 effector cells, it was possible that IFN-γ might promote Th1 cell development by up-regulation of the IL-12Rβ2 molecule while simultaneously inhibiting Th-17 cell differentiation by down regulation of the IL-23R molecule. To examine this scenario, IL-23R expression IFN-γ-deficient CD4+ T cells differentiated toward a Th-17 phenotype in the presence of IL-23, FIG. 6a shows the differential expression of IL-12R and IL-23R by TH1 and Th-17 polarized effector cell populations. Cells were prepared as described in FIGS. 4a and b. The fold-decrease in IL-23 mRNA by IFN treatment was determined by comparison of CD4+ T cells polarized only with IL-23 (in parentheses). The right hand column indicates the priming conditions and percentage of cells expressing IL-17 as determined by intracellular staining as described. Compared with cells treated with IL-23 alone, there was a decrease of 41% in IL-23R expression in association with suppression of Th-17 cell development by exogenous IFN-γ, which was further enhanced (90% decrease) when both IFN-γ and IFN-α were included in the cultures (FIG. 6a). Moreover, IFN-γ neutralization during IL-23 stimulation of CD4+ T cells, in contrast to IL-23 stimulation alone, resulted in a 2.5× increase in IL-23R expression (data not shown).

To further evaluate this mechanism, the expression of IL-12Rβ2 and IL-23 mRNA by real-time PCR in Th1 and Th-17-polarized effector cell generated from naive IFN-γ-deficient CD4+ T cells. IFN-γ-deficient T cells were polarized towards Th1 with IL-12 or Th-17 with IL-23 as described in FIG. 4c. After 5 days in culture, cells were activated for 5 hours with PMA and ionomycin and mRNA was isolated. Relative differences between the two cell populations were determined with the $\Delta\Delta C^t$ method. Values to the left represent more mRNA in Th1 cells, while values to the right indicate more mRNA in Th-17 cells. Th-1-polarized effector cells expressed about threefold more IL-12Rβ2 than did Th-17-polarized cells. In contrast, Th-17-polarized cells expressed about sevenfold more IL-23R than Th1-polarized cells, Thus, in the absence of IFN-γR signaling, the addition of IL-12 and IL-23 was associated with differential expression of IL-12Rβ2 and IL-23R. These data are consistent with a mechanism of Th1-Th-17 lineage divergence in which STAT1 signaling induced by interferon acts to differentially regulate the inducible components of the IL-12R and IL-23R complexes.

IL-4 Suppresses Th-17 Development Independently of INF-γ

Figure 7:
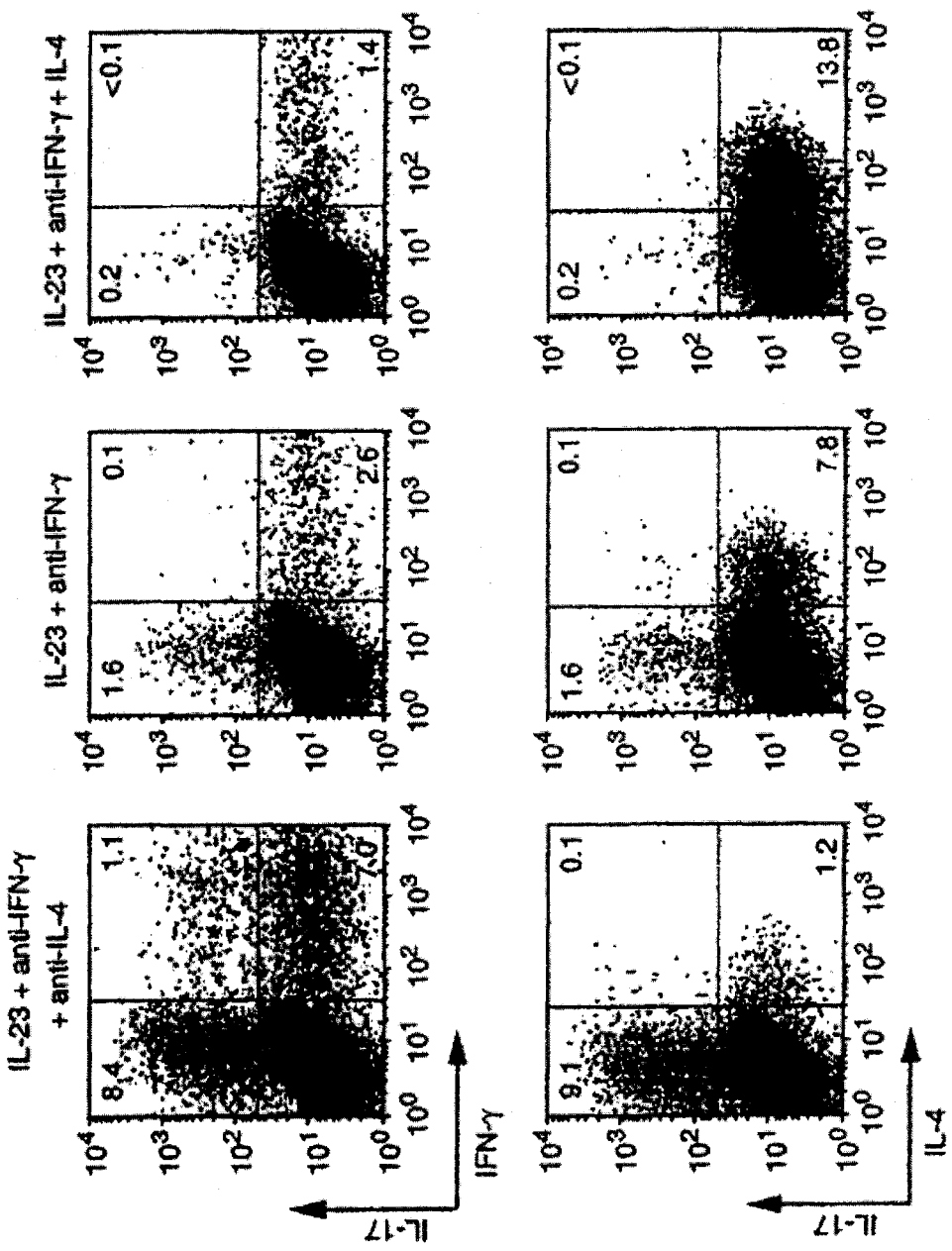
FIG. 7 demonstrates that the Th2-associated signaling molecule IL-4 suppresses cell development independently of INF-$\gamma$.

In the experiments reported above, effector development was initiated in IL-4 neutralizing conditions to locus on the relationship between Th1 and Th-17 cell development, To examine the possibility that IL-4, and thus Th2-polarizing conditions, might preclude Th-17 cell development, the frequency of IL-17 effector cells that developed from antigen-activated DO11.10 cells in IFN-γ neutralizing conditions, with or without exogenous IL-4 or anti-IL-4 were compared. In FIG. 7 DO11.10 TCR-transgenic CD4+ T cells were activated with OVA peptide pulsed splenic feeder cells in the presence of IL-23 and anti-IFN-γ, supplemented with IL-4 or anti-IL-4. After 5 days incubation, CD4+ T cells were collected and stimulated with PMA and ionomycin for 5 hours followed by staining for intracellular IL-17 and IFN-γ (top) or IL-17 and IL-4 (bottom). Plots are gated on CD4+ T cells with numbers in the quadrants indicating the frequency of cells in staining positive for each cytokine. In the absence of IL-4 neutralization, Th-17 cell development was notably blunted compared with that in control conditions in which both IFN-γ and IL-4 were neutralized (1.6% versus 8.4% IL-17, respectively). The addition of exogenous IL-4 further suppressed Th-17 cell development while enhancing Th2 cell development. Thus, IL-4-mediated Th2 cell development precludes cell development.

Th-17 Development is Independent of STAT-4 or STAT-6

Figure 8:
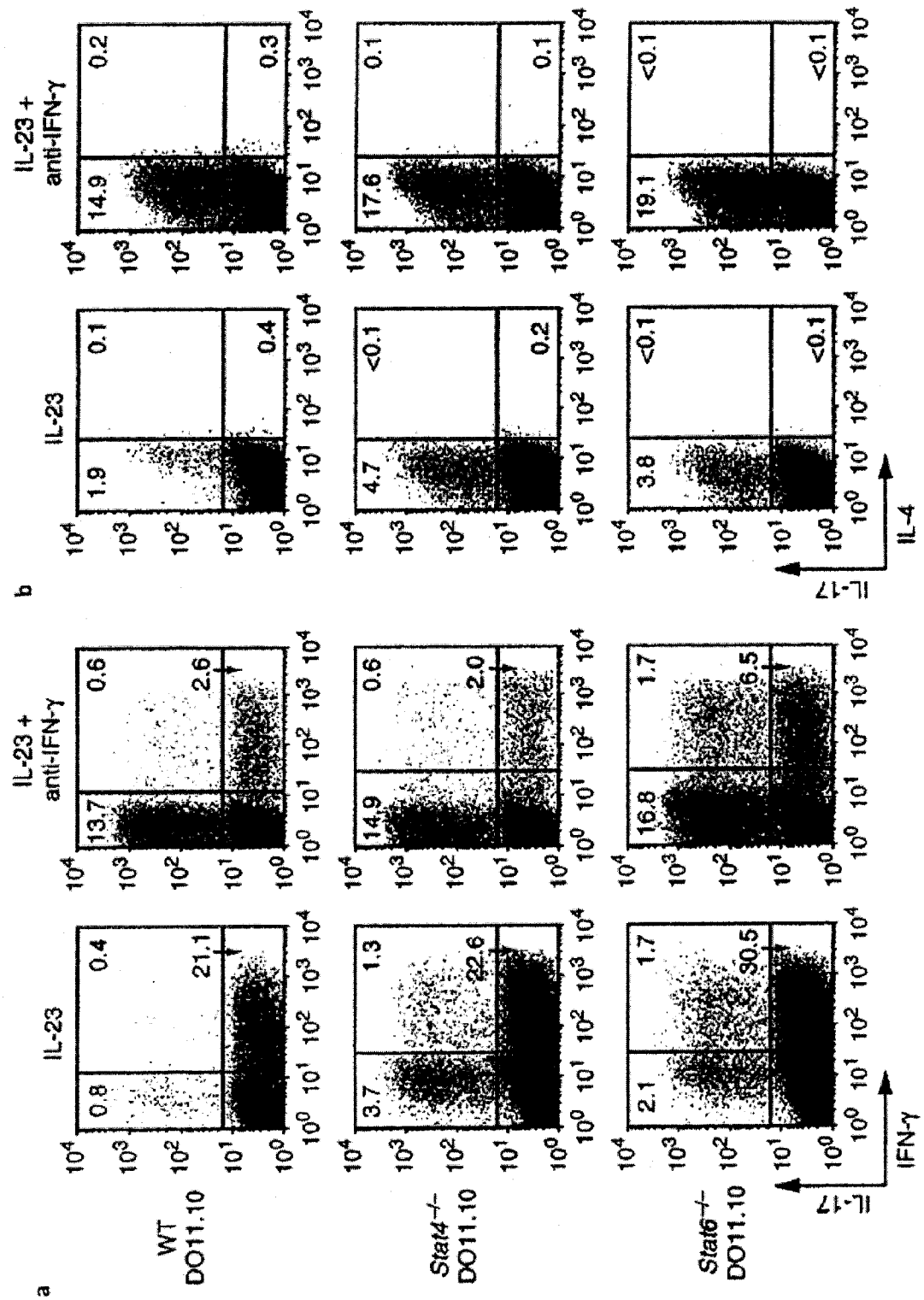
FIG. 8 demonstrates that STAT4 and STATE signaling are not required for IL-17 producing effector cell (Th-17) development.

The optimal differentiation of CD4+ T cells into Th1 or Th2 effector cells requires the action of STAT4 and STAT6, respectively. STAT4 is activated by IL-12 in developing Th1 cells and has also been linked to IL-23 signaling, perhaps through the conserved action of the shared IL-12Rβ chain. Although the experiments reported above indicated distinct proximal developmental programs for the Th1, Th2 and Th-17 cell lineages, this did not preclude the possibility of a shared function for the STAT4 pathway in Th1 and Th-17 cell development. To directly address the involvement of STAT4 in Th-17 cell development, CD4+ T cells from DO11.10 (wild-type), DO11.Stat4–/– (STAT4-deficient) or DO11.Stat6–/– (STAT6-deficient) TCR-transgenic mice were activated with OVA peptide pulsed BALB/c feeder cells and IL-23, with or without anti-IFN-γ. After 5 days primary stimulation, CD4+ T cells and re-stimulated with PMA and ionomycin for 5 hours before intracellular cytokine staining for IFN-γ and IL-17 (FIG. 8a) or IL-4 and IL-17 (FIG. 8b) Data are generated on KJI-26+ CD4+ T cells with the numbers in quadrant indicating the percentage of cells in each. Data presented are representative of two experiments. Activation of wild-type DO11.10 T cells in the presence of IL-23 induced a small fraction of IL-17 producing T cells that was augmented considerably (an increase in frequency of about ten-fold) by the neutralization of IFN-γ, FIG. 8a)—Consistent with previous data (FIGS. 1-3), the IL-17+ and IFN-γ+ T cell populations were mostly distinct and the Th-17 cells did not produce IL-4 (FIG. 8b). A similar pattern of cytokine expression was induced in both STAT4- and STAT6-deficient T cells. Approximately 5% of the STAT4-deficient T cells made IL-17; neutralization of IFN-γ increased this to 15-17% of T cells. The frequency of IL-17+ T cells that developed from STAT6-deficient T cells was comparable to that of STAT4-deficient T cells, with about 3.8% of STAT-6-deficient T cells expressing IL-17 after stimulation with IL-23 alone and more than 18% of STAT-6-deficient T cells expressing IL-17 after stimulation with IL-23 with the addition of ant-IFN-γ. As noted with Th-17 cells derived from wild-type DO11.10 precursor cells, most IL-17-producing Th-17 cells derived from both STAT4- and STAT6-deficient precursor cells were negative for IFN-γ and IL-4 expression. Thus, neither STAT4 of STAT6 signaling is required for Th-17 cell development.

Mature Th-17 Effector Cells are not Inhibited by INF-γ or IL-4

Figure 9:
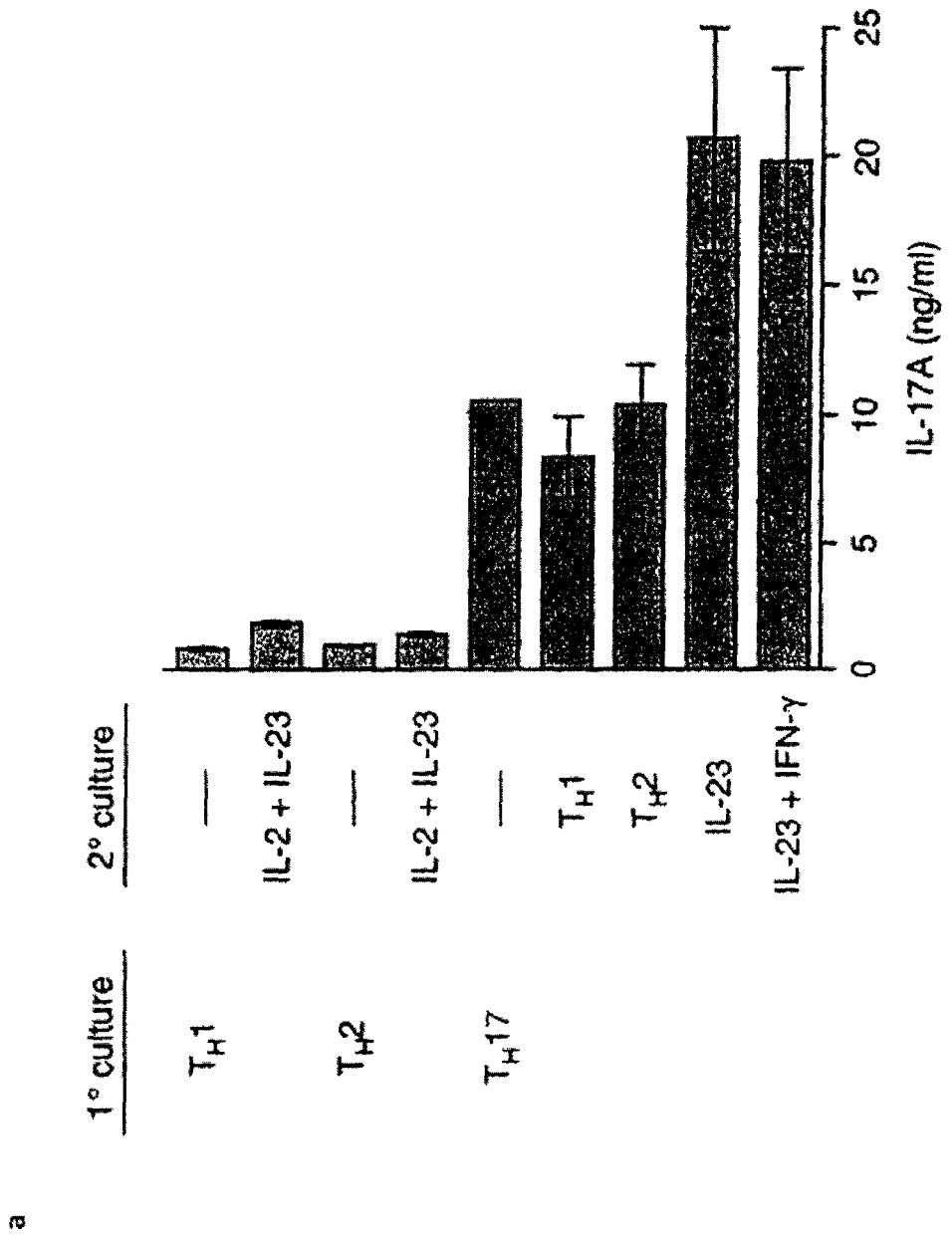
FIG. 9 shows that committed Th-17 effector cells have a stable phenotype when challenged with Th1- and Th2-polorizing conditions.
Figure 9:
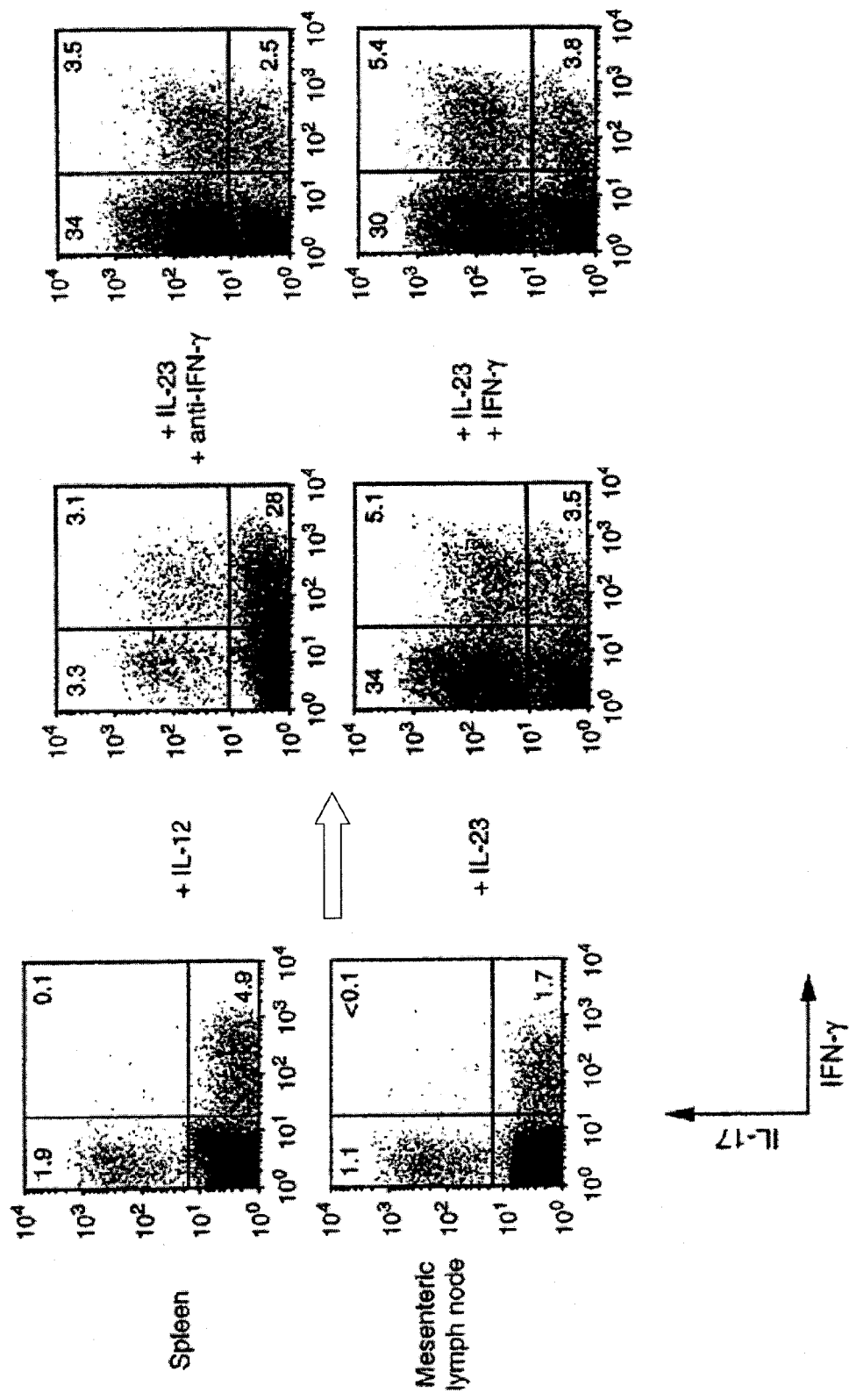

A hallmark of fully differentiated Th1 and Th2 cells is their phenotypic stability; mature Th1 cells re-stimulated in Th2-polarizing conditions do not 'extinguish' IFN-γ expression or acquire the ability to produce IL-4, and vice versa. Given the potent effects of IFN-γ in Th-17 cell development from naive precursor T cells, experiments were conducted to determine whether mature Th-17 cells was also susceptible to suppression by IFN-γ, IL-12 or IL-4 or instead represented a stable phenotype analogous to Th1 and Th2 cells. In FIG. 9a, effector CD4+ T cells were generated in primary culture for 5 days in Th1-polarizing conditions (IL-12 and anti-IL-4), Th2-polarizing conditions (IL-4, anti-IL-12 and anti-IFN-γ) or Th-17-polarizing conditions (IL-23, anti-IFN-γ and anti-IL-4) (designated $1^0$ culture). The cells were recovered and incubated 72 hours in the secondary condition ($2^0$ culture) after which IL-17 production was determined by ELISA. The error bars represent the mean±s.d. of triplicate cultures. Th-17-polarized cells were generated in primary cultures and re-stimulated in the presence or absence of exogenous IFN-γ, Th1- or Th2-polarizing conditions. For comparison, Th-17-, Th1- or Th-2 polarized cells were re-stimulated with or without exogenous IL-23. In accordance with the results presented on intracellular cytokines (FIG. 1), Th1 and Th2 cells re-stimulated with IL-23 produced less IL-17 than did Th-17 polarized cells. The re-stimulation of Th-17 cells in either Th1- or Th-2 polarizing conditions did not induce substantial differences in IL-17 (FIG. 9a). Moreover, Th-17 cells re-stimulated with IL-23 secreted more IL-17 than those not treated with IL-23. The IL-23 induced IL-17 expression was not suppressed by the addition of IFN-γ. Thus, IL-17 production by in vitro-derived, mature Th-17 cells is resistant to suppression by Th1 or Th2 cytokines.

In separate studies, it was determined that whereas a minor fraction of IL-17-competent CD4+ T cells resided in secondary lymphoid tissues of nominal mice (<0.5% of total CD4+ T cells), this population was increased in IL-10-deficient mice before their development of spontaneous colitis (FIG. 9b, and data not shown). These cells were used as a source of in vivo-derived Th-17 effector cells with which to explore phenotype stability. Stimulation of total CD4+ T cells pooled from spleen and mesenteric lymph nodes of IL-10-deficient mice in the presence of exogenous IL-23 led to an increase of about 30-fold its the frequency of IL-17-producing cells after 6 days in culture, without a comparable effect on the fraction of T cells producing IFN-γ (FIG. 9b). Activation of the same population with exogenous IL-12 induced a reciprocal pattern of cytokine expression, with considerable polarization toward the Th1 phenotype. Notably, neither the neutralization of endogenous IFN-γ nor the addition of exogenous IFN-γ had a substantial effect on the phenotype induced by IL-23 (FIG. 9b). These data indicate that unlike naive CD4+ T cells, mature Th-17 effector cells are resistant to the inhibitory effects of IFN-γ and IL-4, consistent with their acquisition of a stable phenotype. This further suggests that the considerable expansion of Th-17 cell populations noted in the presence of IL-23 was probably due to the selective outgrowth of mature Th-17 cells. Therefore, suppression of Th-17 cell development by IFN-γ and IL-4 is limited to an early stage of the Th-17 differentiation process.

TGF-β1 is Required for Optimal Th-17 Development

Figure 10:
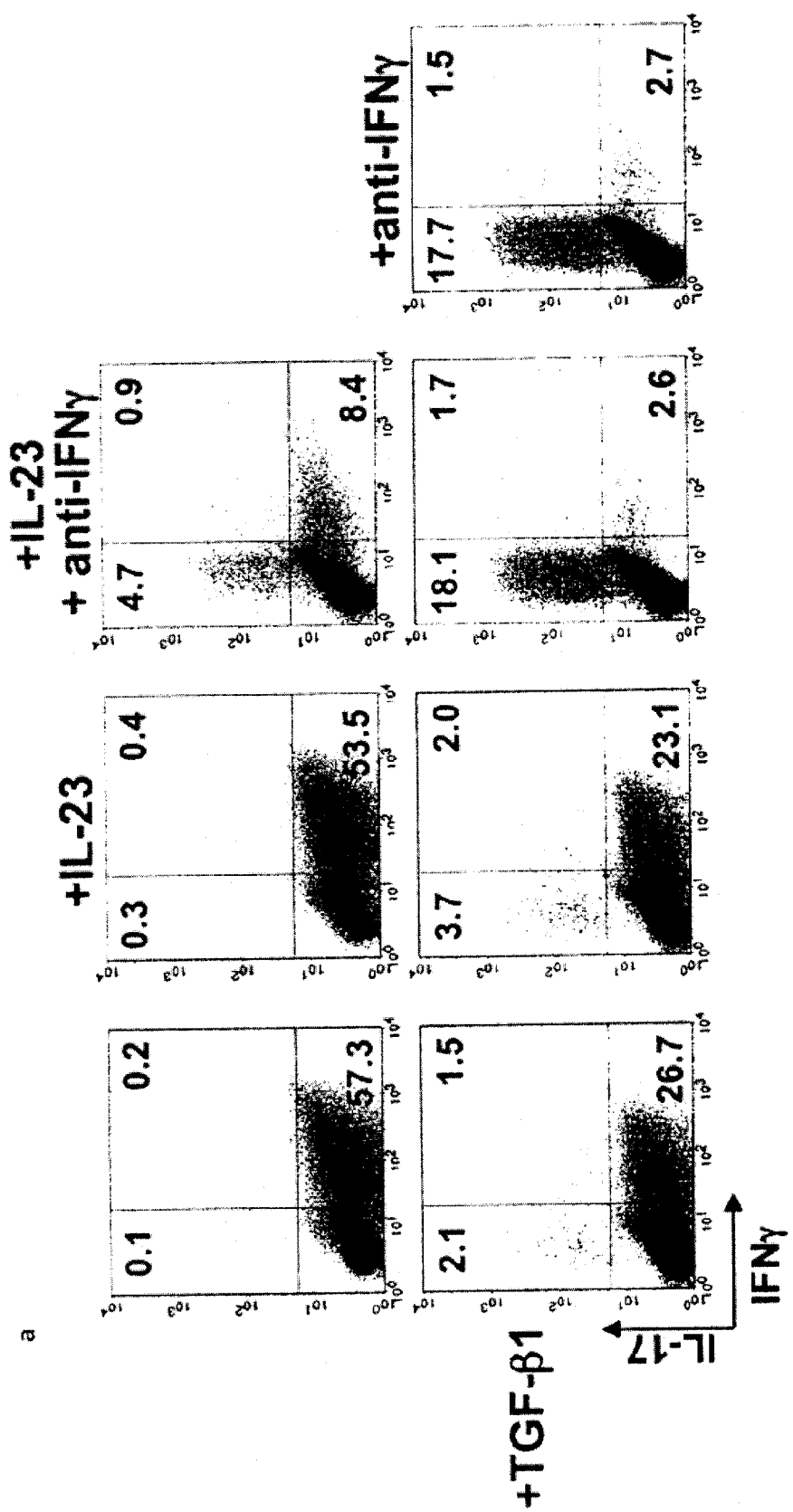
FIG. 10 shows that TGF-$\beta$1 is required for Th-17 commitment independently of IL-23 and that IFN-$\gamma$ (and IL-4 inhibit TGF-$\beta$1 induced differentiation.
Figure 10:
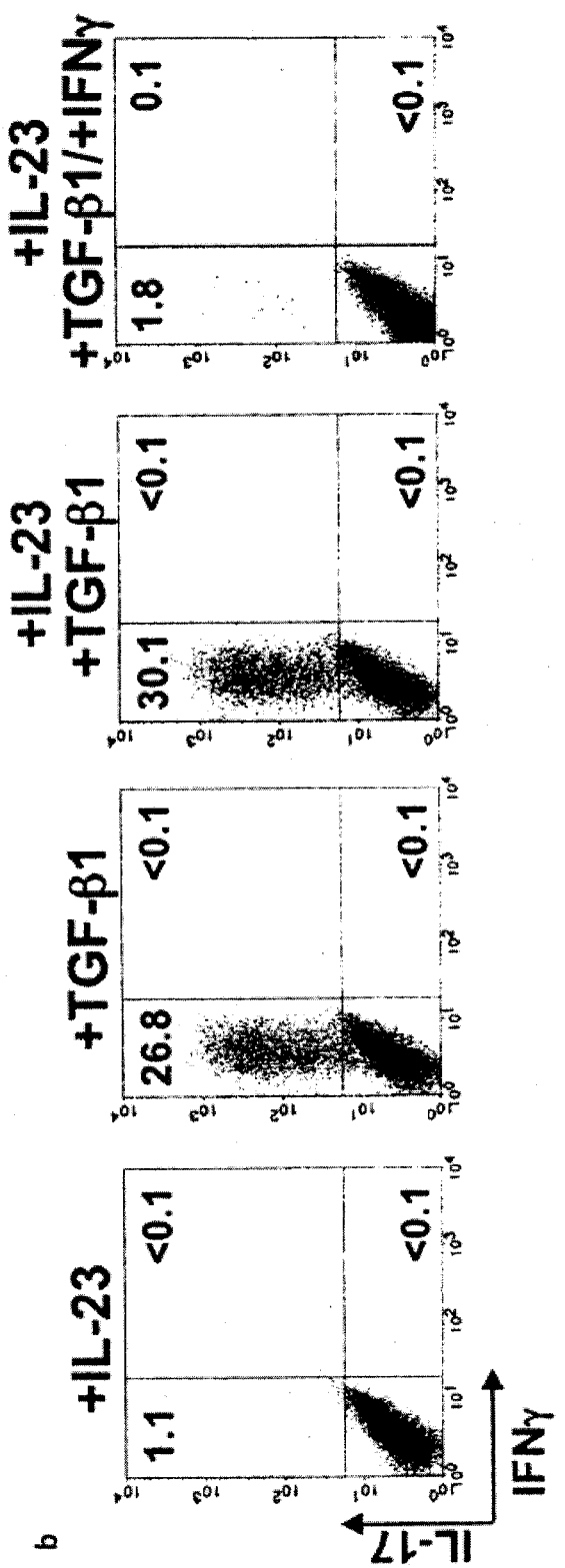
Figure 10:
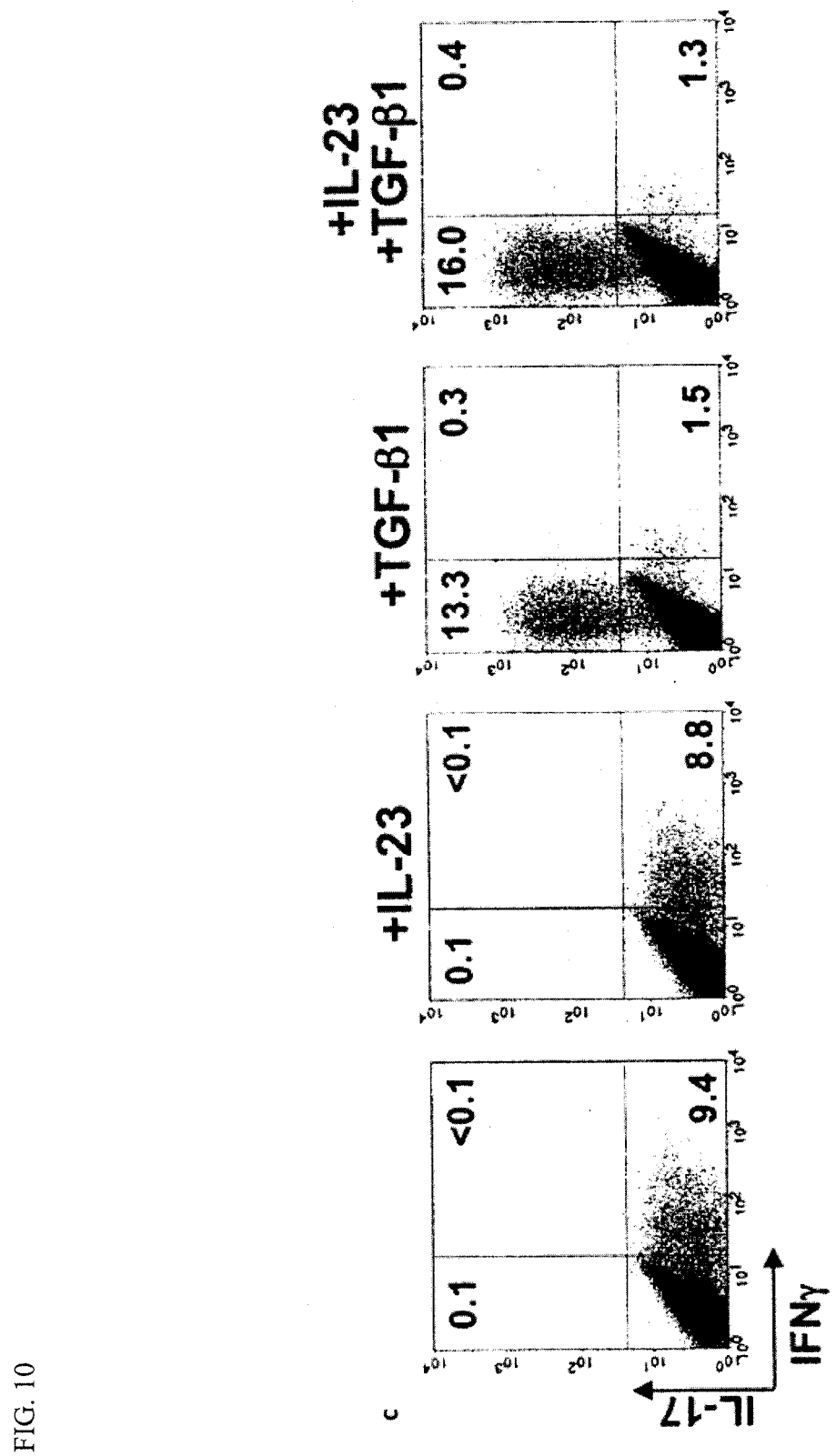
Figure 10:
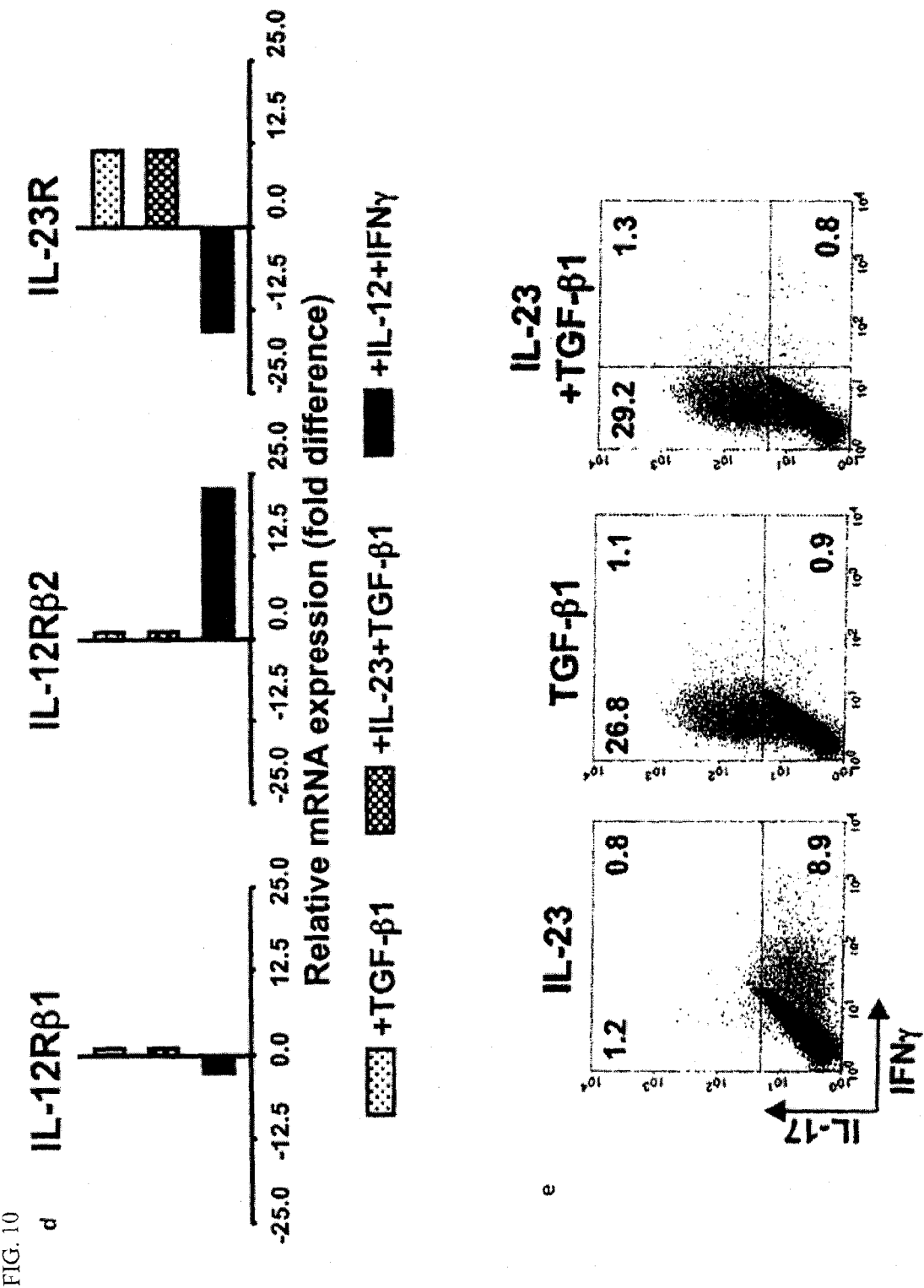

IFN-γ potently inhibits Th-17 development as discussed above (Harrington, Nature Immunol., 6:1123 (2005); Park, Nature Immunol., 6:1133 (2005)). Given the suppressive actions of TGF-β on IFN-γ production (Laouar, Nature Immunol., 6:600 (2005); Lin, J. Immunol., 174:5950 (2005); Li, Annu. Rev. Immunol., 24:99 (2006)), TGF-β may contribute to Th-17 development by limiting inhibitory actions of IFN-γ or by stimulating directly Th-17 development in some manner. To examine these possibilities, naive CD4+ T cells were activated under Th2-neutralizing conditions under controlled availability of IL-23 and IFN-γ, with or without exogenous TGF-β1, and cytokine phenotypes of the resulting cells were examined. The results are shown in FIG. 10.

In these experiments, naive CD4+ T cells were isolated from DO11.10 T-cell receptor (TCR) transgenic mice and activated with OVA peptide and cytokines under the indicated conditions indicated in FIG. 10a and as described in the Methods section and in Mangan, Nature, 441:231 (2006). T cells were recovered after 6 days of indicated treatment and re-stimulated with PMA plus ionomycin for 5 h with monensin block before intracellular cytokine staining for IL-17 and IFN-γ, and analysis by flow cytometry. Plots are gated on CD4+ cells and the quadrant percentiles of cells staining positively for the indicated cytokines are shown.

Consistent with the results discussed above, the addition of IL-23 (10 ng/ml) did not substantially enhance development of IL-17+ cells unless endogenous IFN-γ was neutralized (FIG. 10a, top panel). Addition of TGF-β1 (5 ng/ml) alone reduced the fraction of IFN-γ+ T cells by more than two-fold and induced the development of a small, but appreciable, fraction of IL-17+ cells (FIG. 10a, bottom panel). In the presence of exogenous IL-23, TGF-β1 suppressed IFN-γ induction similarly to that in the absence of added IL-23, while modestly increasing IL-17+ cells. Under conditions of IL-23 addition and IFN-γ neutralization, exogenous TGF-β1 induced further suppression of IFN-γ+ cells compared to that of IL-23 addition alone and, notably, induced a markedly increased fraction of IL-17+ cells. A similar induction of IL-17+ cells was found irrespective of exogenous IL-23 addition. These data indicate that in addition to its inhibitory effect on Th1 development, TGF-β1 promotes development of Th-17 cells.

To determine whether the augmenting effects of TGF-β1 were due to the enhanced suppression of IFN-γ or also to IFN-γ-independent mechanisms, the effects of exogenous TGF-β1 on Th-17 development under IFN-γ-null conditions were examined. Naive CD4+ T cells from Ifng −/− mice were cultured with irradiated Ifng −/− splenocytes, anti-CD3 monoclonal antibody and anti-IL-4 (Th2 neutralizing conditions), with IL-23 and/or TGF-β1, as indicated in FIG. 10b. T-cells were recovered an analyzed as described in FIG. 10a. IFN-γ was included in cultures where indicated. The results are shown in FIG. 10b.

Addition of IL-23 alone induced few IL-17+ cells consistent with the results above, indicating that in the absence of IFN-γ, IL-23 alone is insufficient to promote robust Th-17 development. Addition of TGF-β1 promoted a substantially increased fraction of IL-17+ cells, which was only modestly augmented by co-addition of exogenous IL-23. Therefore, TGF-β1 can act independently of IFN-γ blockade to promote Th-17 development. Notably, reconstitution of IFN-γ deficient cultures with high levels of exogenous IFN-γ strongly inhibited Th-17 development despite abundant TGF-β1 and IL-23.

Figure 11:
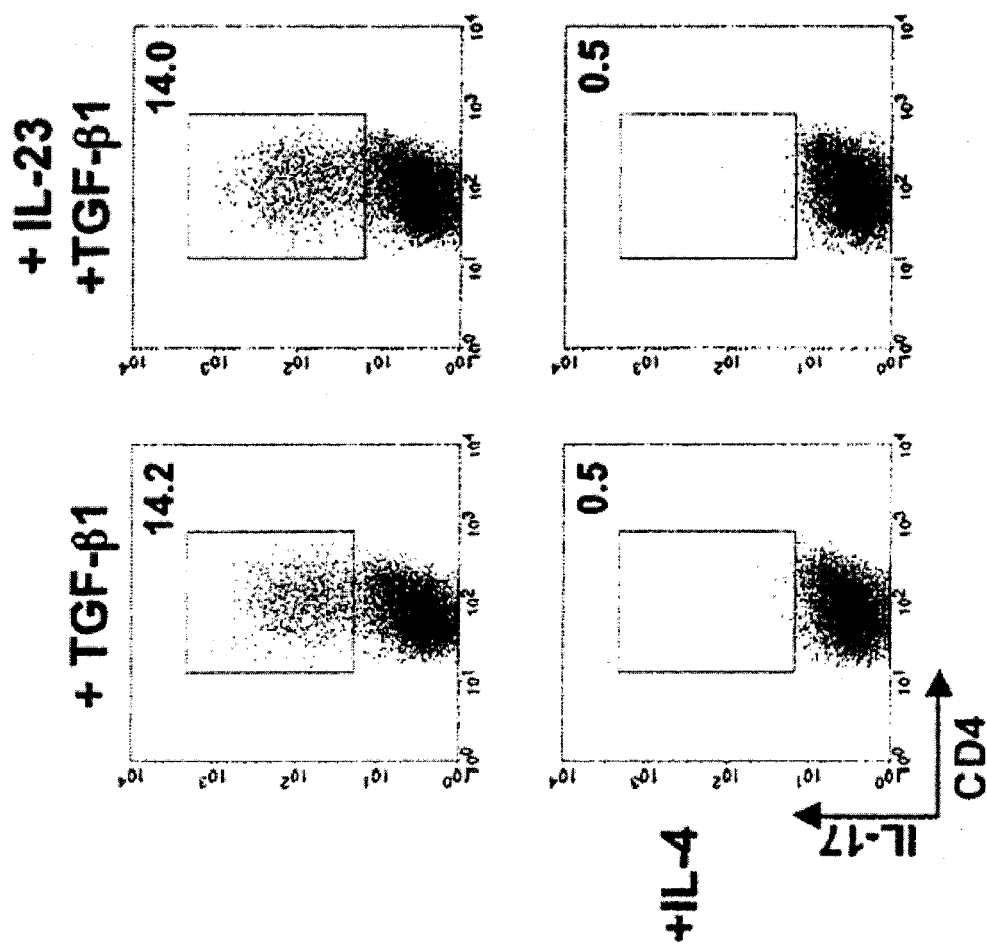
FIG. 11 further demonstrates that induction of Th-17 development is independent of IL-23.

Furthermore, TGF-β1-induced Th-17 differentiation is inhibited by IL-4. Naïve B6 CD4+ T cells were cultured with wild-type B6 splenocytes and activated with anti-CD3 antibody, in the presence of anti-IFN-γ or anti-IL-4 neutralizing antibodies (10 µg/ml each). TGF-β1 (5 ng/ml) was added alone or in combination with IL-23 (10 ng/ml), as indicated. Where indicated, IL-4 (1000 U/ml) was included, and neutralizing anti IL-4 antibody was omitted. After 6 d in culture, T cells were re-stimulated and analyzed by flow cytometry as described in FIG. 10a. The results are shown in FIG. 11. Values indicate the frequency of CD4+ T cells contained within the designated region.

Therefore, the results above indicate that TGF-β, IFN-γ and IL-4 act antagonistically to specify Th-17, Th1 or Th2 development, respectively.

TGF-β1 Induced Th-17 Differentiation Independently of IL-23

Although the foregoing experiments identified an essential role for TGF-β1 in Th-17 development, they did not exclude the possibility that TGF-β1 acts together with endogenous IL-23. In order to examine this possibility, splenocytes from IL-12p40-deficient (Il12b −/−; hereafter called p40 −/−) mice as a source of IL-23 (and IL-12)-deficient antigen presenting cells (APCs) in order to examine Th-17 development under defined conditions of IL-23 availability. Naive CD4+ T cells were isolated from wild-type (B6) mice and cultured with p40 −/− splenocytes and anti-CD3, anti-IL-4 and anti-IFN-γ. Cultures were supplemented with nothing or IL-23 and TGF-β1 added alone or in combination. After 6 days in culture, T cells were re-stimulated and analyzed by flow cytometry as described in FIG. 10a. The results are presented in FIG. 10c.

Without IL-23 and exogenous TGF-β1, few IL-17-producing T cells were generated, and IL-23 alone did not restore Th-17 development (FIG. 10c). Surprisingly, addition of TGF-β1 was sufficient to induce robust Th-17 development in the absence of IL-23, and development of IL-17-producing T cells was only modestly enhanced by co-addition of IL-23. Under more stringent conditions of IFN-γ signaling deficiency, in which IFN-γ receptor-1-deficient (Ifngr −/−) T cells were used, more striking TGF-β1-dependent, IL-23-independent Th-17 development was observed. In this experiment, naïve CD4+ T cells were isolated by FACS from IFN-γ receptor 1-deficient (Ifngr −/−) mice and cultured with IL-12p40-deficient (Il12b −/−) splenocytes and anti-CD3, under Th2-neutralizing conditions. Cultures were supplemented with IL-23 and TGF-β1, added alone or in combination as indicated in FIG. 10e. Without IL-23 and exogenous TGF-31, few IL-17-producing T cells were generated, and IL-23 alone did not restore Th-17 development (FIG. 10c). Again, addition of TGF-β1 was sufficient to induce robust Th-17 development in the absence of IL-23 and to a greater extent than when IFN-γ signaling was not interrupted. Again, the development of IL-17-producing T cells was only modestly enhanced by co-addition of IL-23. Therefore, TGF-β1 acts independently of IL-23 to induce Th-17 lineage commitment.

TGF-β1 Induced IL-23 Receptor Expression

The IL-23 receptor is a heterodimer of IL-12Rb1, which is constitutively expressed by naive T cells, and IL-23R, which is not. In view of the foregoing results, TGF-β1 might act proximally in Th-17 development to induce IL-23R up-regulation, analogous to the induction of IL-12Rb2 by IFN-γ during Th1 development (Berenson, Immunol. Rev., 202:157 (2004)). In order to examine this possibility, the expression of IL-12 and IL-23 receptors during Th1 or Th-17 development was compared.

Naive CD4+ T cells from Ifng −/− mice were activated were activated with Ifng-1-splenocytes and anti-CD3 plus anti-IL-4 (neutral cytokine conditions), or under Th-17-polarizing (TGF-β1 alone, TGF-β1 plus IL-23) or Th1-polarizing (IFN-γ plus IL-12) conditions, and relative expression of IL-12Rβ1, IL-12Rβ2 and IL-23R messenger RNA determined. The results are shown in FIG. 10d. After 6 days, T cells were collected and processed for mRNA quantification by real-time RT-PCR as described in the Methods section. Data shown are fold differences relative to T cells from a culture that was differentiated under non-polarizing (neutral) conditions (that is, was not supplemented with cytokines). Compared to neutral conditions, Th-1 polarization induced IL-12Rβ2 expression while inhibiting IL-23R expression. In contrast, addition of TGF-β1 induced IL-23R expression, irrespective of IL-23 addition. Thus, TGF-β1 and IFN-γ differentially induce mRNA for IL-23 and IL-12 receptors, respectively. Therefore, the results indicate that TGF-β1 thereby acts proximally in Th-17 development to confer IL-23 responsiveness.

In Vivo Development of an IL-17 Effector Response to a TH17-Dependent Pathogen is IL-23-Independent, but Protection is IL-23-Dependent The foregoing results show a central role for TGF-β in the initiation of Th-17 differentiation and placed TGF-β signaling proximal to IL-23 receptor expression and signaling in the Th-17 developmental program. To confirm and extend these findings in vivo, a natural rodent pathogen, *Citrobacter rodentium* (14), for which an intact IL-23-IL-17 axis seems to be essential for host protection was used. In immunocompetent mice, *C. rodentium* induces a transient, distal colitis with resolution of lesions and clearance of the bacteria after 14-21 days, after induction of a systemic, CD4+ T-cell-dependent IgG response (15-17). Although previously associated with Th1 adaptive immunity (18), oral challenge with this organism induced a potent Th-17 response that was associated with host protection.

Figure 12:
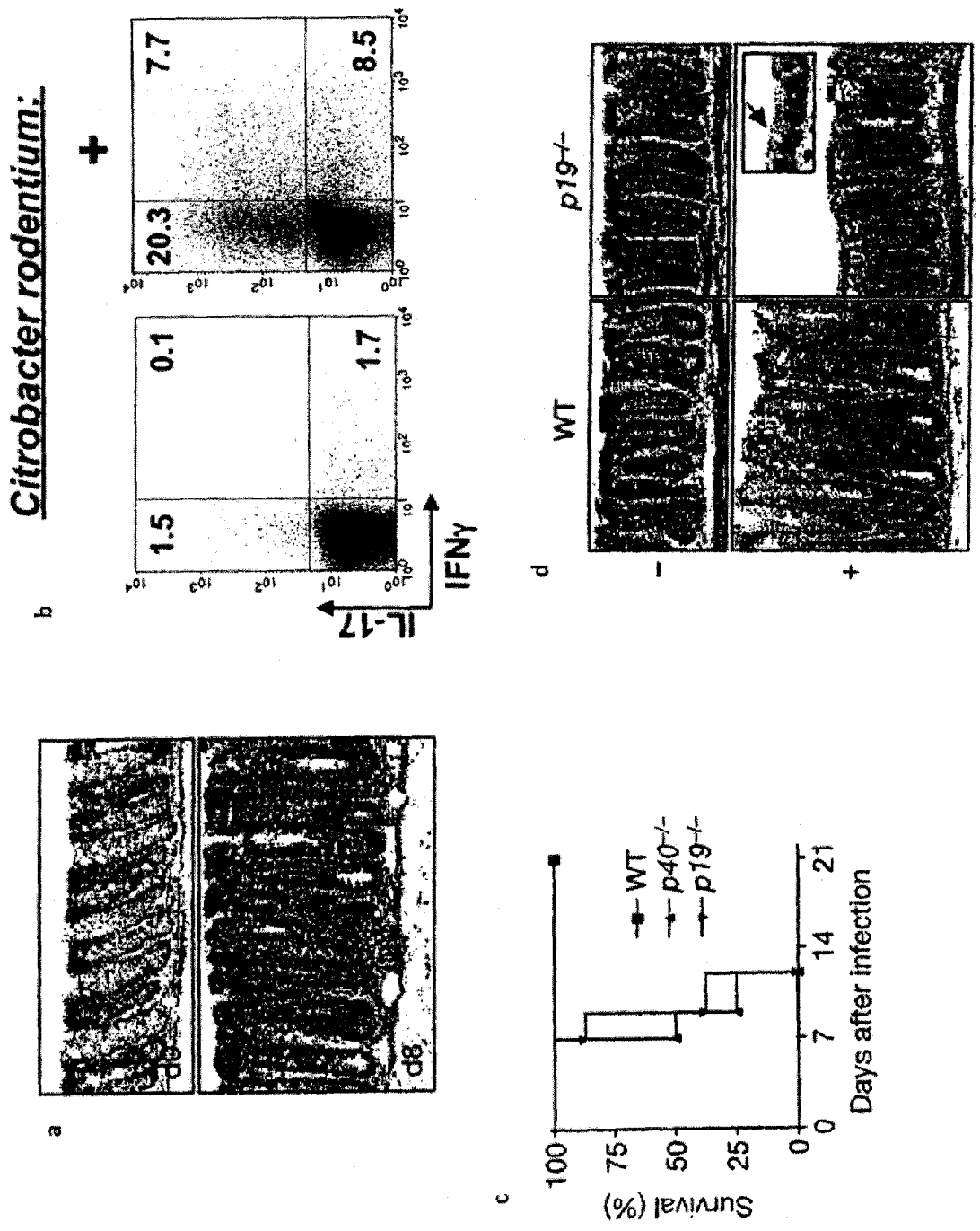
FIG. 12 shows that in vivo development of an IL-17 effector response to a Th-17-dependent pathogen is IL-23-independent, but protection is IL-23-dependent.
Figure 12:
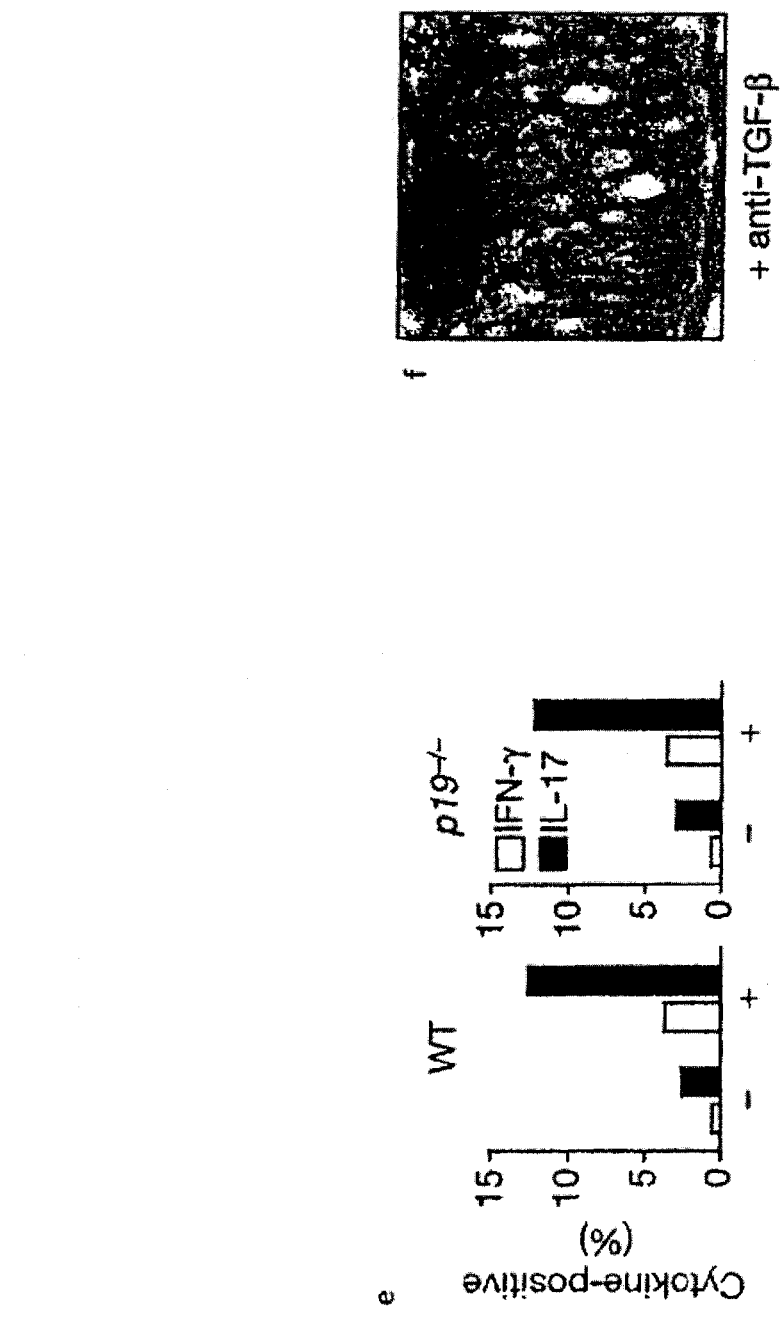

The *C. rodentium* model was used as described in the Methods section. FIG. 12a shows histopathology of distal colon of B6 (wild-type) mice inoculated orally with $1\text{-}2\times10^9$ CFU *C. rodentium* and analyzed before colonization (day 0), or at the peak of infection (day 8). At the peak of inflammation, 8 days after inoculation (FIG. 12a), a large fraction of colonic CD4+ T cells expressed IL-17. In contrast, FIG. 12b shows a lower frequency of cells that expressed IFN-γ a day after inoculation. In FIG. 12b, the cytokine phenotype of lamina propria lymphocytes isolated from B6 mice sham infected (−) or infected (+) with *C. rodentium* as described in FIG. 12a. Recovered cells (8 days after inoculation) were processed for FACS as described in the Methods section and FIG. 10.

Mice deficient in IL-23 (p19 −/−) but able to produce IL-12 failed to clear the infection, and uniformly succumbed at a rate comparable to mice deficient for both IL-12 and IL-23 (p40 −/−). FIG. 12c illustrates the survival analysis of wild-type (n=5), p40 −/− (n=4) and p19 −/− (n=8) mice after infection with *C. rodentium* as in above. Although uninfected wild-type and IL-23-deficient mice had similar baseline histological features, the latter developed significantly less colonic inflammation after infection (FIG. 12d), despite impaired bacterial clearance. FIG. 12d shows histopathology of day 8 colonic tissues from sham-infected (−) or *C. rodentium* infected (+) mice of the indicated genotypes (WT or p10 −/−). The arrow denotes bacteria adherent to colonic epithelial cells. The induction of an IL-17 response was unimpaired in all examined tissues of infected IL-23-deficient mice, and dominated the IFN-γ response before and after infection (FIG. 12e, and data not shown). Thus, despite an impaired inflammatory response, and deficiencies in bacterial clearance and host protection, IL-23-deficient mice were nevertheless competent to develop a vigorous effector IL-17 response. Therefore, whereas IL-23 is dispensable for the differentiation of IL-17-competent T cells, it is indispensable for a fully effective, protective Th-17 response.

To determine whether TGF-β deficiency impaired Th-17 development in vivo, the effect of anti-TGF-β neutralizing antibody on the course of *C. rodentium* infection was examined. FIG. 12f shows histopathology of day 8 colonic tissue from *C. rodentium*-infected p19 −/− mice treated with anti-TGF-β showing severe ulcerative, haemorrhagic colitis induced was by anti-TGF-β treatment. The arrows denote bacteria invading ulcerated colonic epithelium. All sections (except inset) were photographed at the same magnification (×20). IL-23-deficient mice (p19 −/−) treated with anti-TGF-β developed severe ulcerative and haemorrhagic intestinal lesions with gross bacterial invasion, neither of which was found in IL-23-deficient mice treated with an isotype control, or infected wild-type mice (FIG. 12f). This data suggests a critical role for TGF-β in protection against *C. rodentium*.

Development of TH17 Cells is Impaired in TGF-β1-Deficient Mice

Figure 13A:
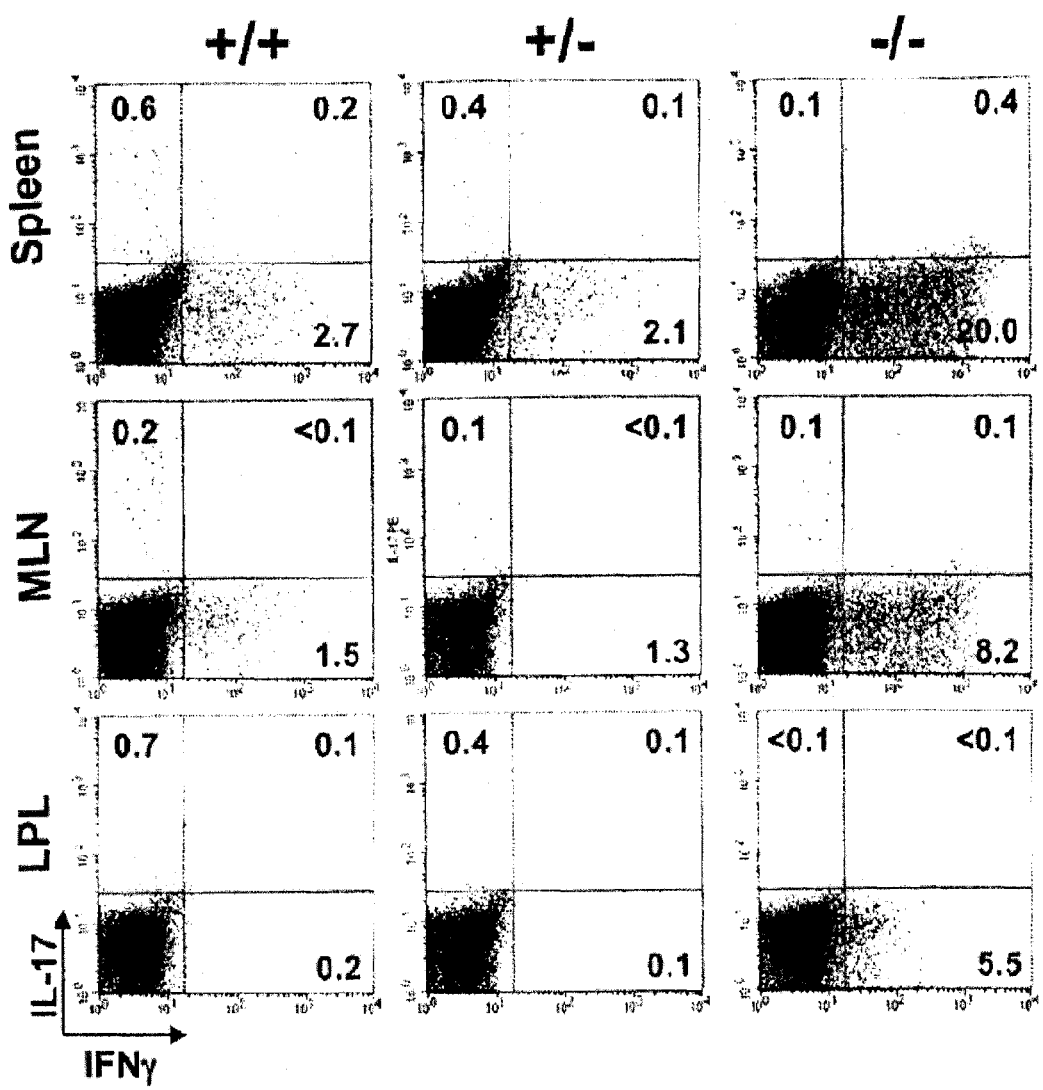
FIG. 13 shows that the development of Th-17 cells is impaired in TGF-$\beta$1-deficient mice.
Figure 13:
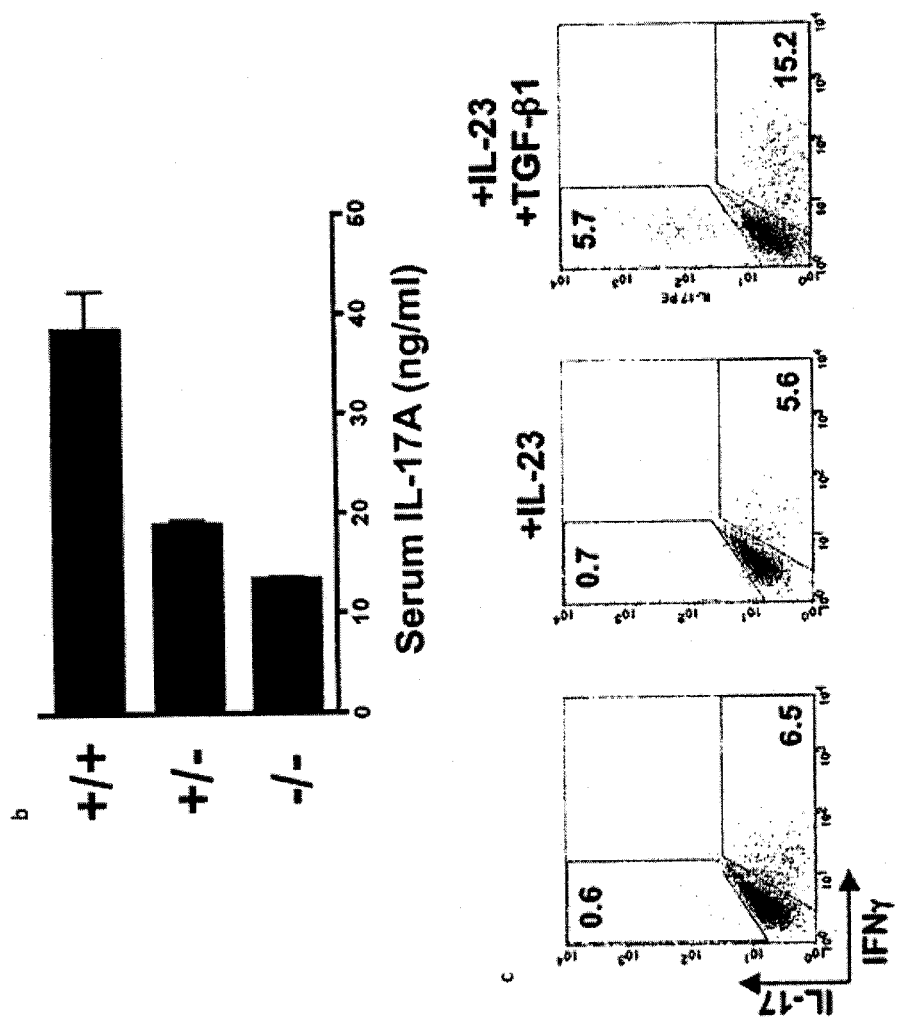

In additional studies, the development of Th-17 cells in TGF-β1-deficient mice (Tgfb1 −/−) in a non-infectious setting was examined. In view of the finding that Th-17 cells were normally enriched in intestinal tissues (FIG. 12), T cells of the gut, as well as peripheral lymphoid tissues, were examined for IL-17 expression. The results are shown in FIG. 13a. CD4+ T cells were purified from the indicated tissues of TGF-β1 −/− mice (−/−), and age-matched hemizygous (+/−) and wild-type (+/+) littermates. Isolated cells were stimulated immediately after isolation with PMA and ionomycin for 5 h before intracellular cytokine staining for IL-17 and IFN-γ. Stained T cells were acquired and analyzed by flow cytometry as in FIG. 10 (MLN designated mesenteric lymph nodes and LPL designates lamina propria lymphocytes). Compared to age- and sex-matched wild-type controls, Th-17 cells were profoundly diminished or absent in all tissue sites of TGF-β1-deficient mice; mice hemizygous for TGF-β1 deficiency (Tgfb +/−) were intermediate. Interestingly, deficiency of IL-17+ cells was associated with significant decreases in basal circulating levels of IL-17 (FIG. 13b), consistent with the predominance of T cells as a source of IL-17 and a major role for the TGF-β1 isoform in controlling homeostatic levels of IL-17 production. Serum from age-matched Tgfb1 −/− mice (−/−), and hemizygous (+/−) and wild-type (+/+) littermates was collected and analyzed for IL-17A by enzyme-linked immunosorbent assay. Data are the mean±s.e.m. of triplicate determinations from 4-8 mice. Furthermore, there was a striking, inverse correlation of IFN-γ-producing cells with TGF-β1 deficiency, in accord with the spontaneous auto-inflammatory syndrome that these mice develop (Shull, Nature, 359:693 (1992); Kulkarni, Proc. Natl. Acad. Sci. USA, 90:770 (1993)). Notably, although fewer naive precursors were present in Tgfb1 −/− mice, there was no intrinsic defect in the ability of these cells to undergo Th-17 development, provided that the high endogenous IFN-γ levels were at least partially neutralized and exogenous TGF-β1 was provided (FIG. 13c). Naive CD4+ T cells were isolated from Tgfb1 −/− mice and activated with CD4 T cell depleted Tgfb1 −/− splenocytes and anti-CD3, with or without added IL-23 and/or TGF-β1. After 6 days, recovered cells were activated with PMA and ionomycin and analyzed for expression of intracellular cytokine. Plots are gated on CD4+ cells and the quadrant percentiles of cells staining positively for the indicated cytokines are shown.

Collectively, these data show a critical function for TGF-β1 in the development of Th-17 cells in vivo.

TGF-β1 Induces IL-17 and Foxp3 Expression by Distinct CD4+ Subpopulations

Figure 14:
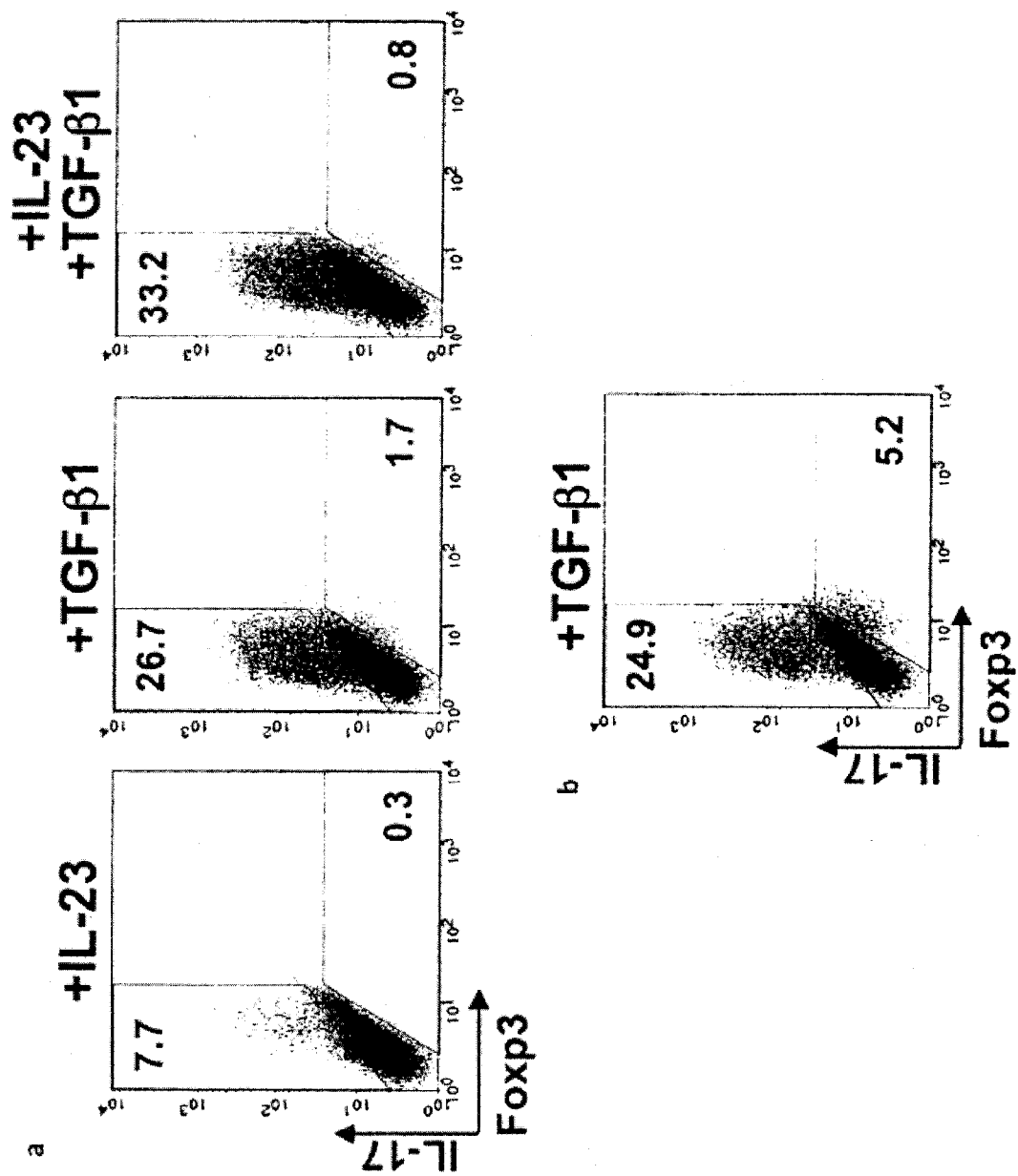
FIG. 14 shows that TGF-$\beta$1 induced IL-17 and Foxp3 expression by distinct CD4+ T cell subpopulations and that IL-6 suppresses TGF-$\beta$-dependent development of Foxp3 T cells.
Figure 14:
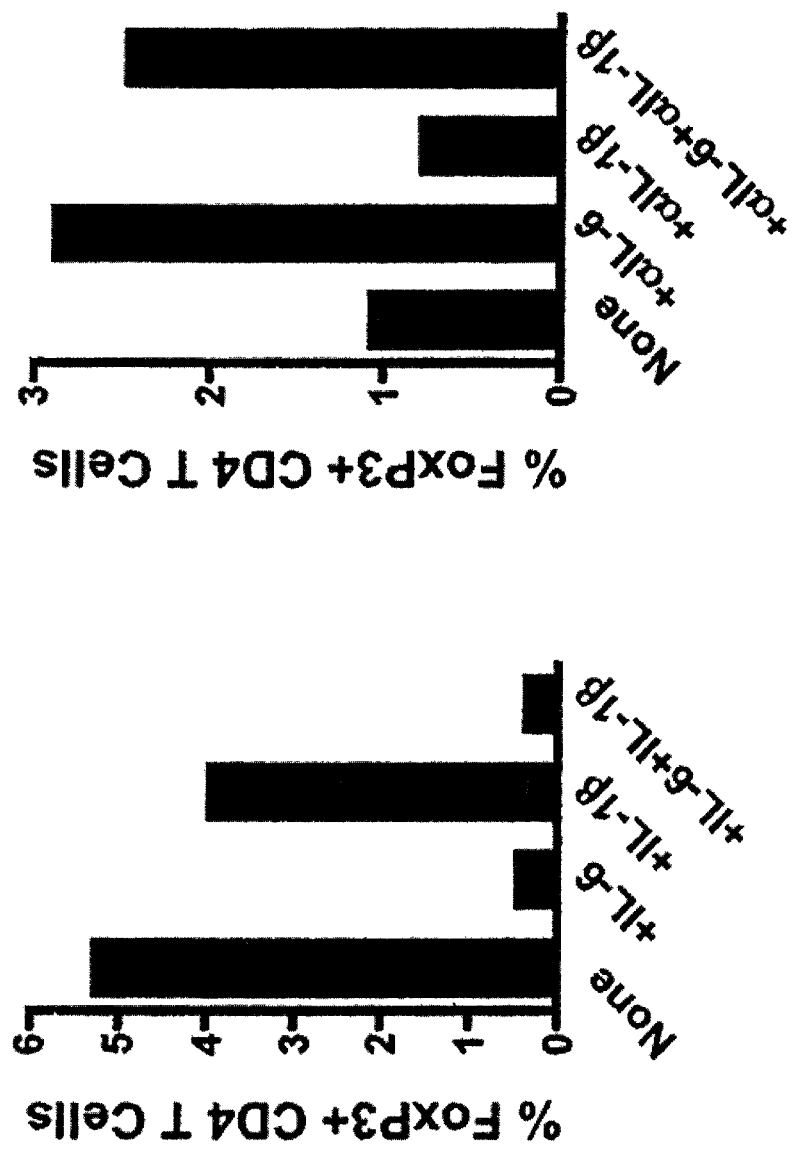

TGF-β1 has been associated with immunosuppression through its inhibitory effect on effector T-cell development (for example, Th1) and its role as an immunosuppressant cytokine produced by some regulatory T (Treg) cells. TGF-β1 also directs the development of Treg cells that express the transcription factor Foxp3 (Chen, J. Exp. Med., 198:1875 (2003); Wan, Proc. Natl. Acad. Sci. USA, 102:5126 (2005)). In order to determine the relationship between Foxp3 and IL-17 expression, TGF-β induced expression of Foxp3 together with IL-17 was examined. Naive T cells were activated in the presence of exogenous TGF-β1 and evaluated for intracellular expression of IL-17 and Foxp3. In FIG. 14a, naïve CD4+ T cells purified from Ifng −/− mice by FACS sorting were co-cultured with irradiated Ifng −/− splenic feeder cells and activated with anti-CD3 under Th2-neutralizing conditions. IL-23 or TGF-β1 was added alone or in combination. In FIG. 14b, naive CD4+ T cells were prepared from wild-type B6 mice and cultured with wild-type splenocytes, anti-CD3, TGF-β1, anti-IFN-γ and anti-IL-4 as in FIG. 14a. After 6 days in culture, T cells shown in FIGS. 14a and b were re-stimulated with PMA and ionomycin before intracellular cytokine staining for IL-17 and Foxp3. Stained T cells were acquired and analyzed by flow cytometry as in FIG. 10. Plots are gated on CD4+ cells and the quadrant percentiles are given for cells staining positively for IL-17 or Foxp3. FIGS. 14a and b shows that distinct subpopulations of IL-17- and Foxp3-expressing T cells developed, albeit with a marked predominance of IL-17-producing T cells, under the conditions examined. As in previous experiments, the effects of exogenous IL-23 were modest in comparison to the effects of TGF-β1 alone. Furthermore, the frequency of Foxp3+ cells generated in the presence of TGF-β was inversely related to levels of IL-6, such that Foxp3+ cells were nearly extinguished in the presence of exogenous IL-6. In FIG. 14c (left panel), naïve CD4+ T cells were cultured with BMDC prepared as described in the Methods section and Kubo, J. Immunol., 173:7249 (2004) and activated with anti-CD3 (2.5 µg/ml) in the presence of TGF-β1 (1 ng/ml) and IL-2 (20 U/ml). Cultures were supplemented with nothing, IL-6 (20 ng/ml), IL-1B (10 ng/ml) or IL-6 and IL-1β as indicated. T cells were recovered on day 4 and re-stimulated with PMA and ionomycin before intracellular staining for Foxp3 and analysis by flow cytometry. Plots are the frequencies of CD4+ Foxp3+ cells. In FIG. 14c (right panel) naïve CD4+ T cells were activated by anti-CD3 and LPS-activated BMDCs as above in the presence of TGF-β and IL-2 as described above. Blocking antibodies to IL-6 (10 µg/ml) and/or IL-1B (33 µg/ml) were added as indicated. Cells were recovered and analyzed as above. As can be seen the addition of IL-6 inhibited the formation of Foxp3 cells. Thus, TGF-β seems to have a dual role in T-cell differentiation by directing distinct subpopulations of Foxp3+ Treg cells and Th-17 cells, contingent upon the inflammatory cytokine environment, perhaps providing a mechanism by which Treg cells are poised to terminate Th-17 responses after antigen clearance.

Global Gene Expression Profiling of Th17 Cells.

To better define gene expression markers of the Th17 lineage and identify potential targets for therapeutic modulation of Th17 function, global gene expression studies were performed to compare genes expressed by naïve CD4 T cells (both activated and unactivated), Th17 cells and Th1 cells. Naive CD4 T cells were isolated from C57B1/6 mice by magnetic sorting for CD4+ cells, followed by FACS sorting for the CD4+CD25−CD62L fraction, which was divided for derivation of four groups: 1) naïve CD4+ (Tn); 2) stimulated naïve CD4+ (Tn*); 3) Th17; and 4) Th1. Naïve CD4+ cells were not further activated, and total RNA was isolated for gene expression analysis. Stimulated naïve CD4+ T cells were activated with PMA and ionomycin under standard conditions for 5 hours, followed by total RNA isolation. Th17 cells were derived by in vitro culture of naïve CD4+ cells for 5 d with IL-12p40-deficient splenic feeder cells, anti-CD3, TGF-β, IL-6, anti-IL-4 and anti-IFN-γ, as described herein and according to the protocols in Harrington et al. (Nature Immunology 6:1123, 2005), followed by stimulation for 5 h with PMA/ionomycin and isolation of total RNA. Th1 cells were derived by culture of naïve CD4+ cells for 5 d with splenic feeder cells, anti-CD3, IL-12 and anti-IL-4, followed by stimulation for 5 h with PMA/ionomycin and isolation of total RNA.

Isolated RNA from all groups was processed identically; biotinylated cDNA was prepared from RNA using a commercial reagent kit and biological duplicates were hybridized to Affymetrix mouse 430 2.0 microarrays. Data was analyzed by the UAB Biostatistics and Bioinformatics Unit, using an expression cut-off of $\log_2$ values>5 and absolute $\log_2$ fold-change values>2 for at least one of six pair-wise cell type comparisons (Th17/Th1, Th17/Tn*, Th17/Tn, Th1/Tn*, Th1/

Tn, Tn*/Tn) after normalization (GCMRA, Bioconductor). Data in Table 1 are representative of 674 genes specifically up-regulated in Th17 vs. Th1 using the cut-off criteria above.

As can be seen from Table 1 a number of genes are upregulated in Th-17 cells as compared to naïve CD4 T cells and Th-1 cells. Such genes include transcription factors, cell signaling molecules, cytokines and cytokine receptors, chemokines and chemokine receptors and genes involved in adhesion and tissue remodeling. The identification of such genes provides therapeutic targets to modulate the function of Th-17 cells. Furthermore, such genes may be used in methods of diagnosis in determining whether a subject is suffering from or at risk from a disease involving Th-17 function Chemokine receptors and chemokines are responsible, at least in part, for migration of activated T-cells into tissues during the inflammatory response. The chemokines are 8-16 kDa soluble proteins produced and released by a wide variety of cell types during the initial phase of host response to injury, allergens, antigens, or invading microorganisms. They selectively attract leukocytes, such as Th-17 cells, to inflammatory foci, inducing both cell migration and activation. Based upon the positioning of their cysteine residues, the chemokines have been classified into the alpha (C-X-C), beta (C-C), and the gamma (C) subgroups. The mechanism of chemokine action involves initial binding to specific seven transmembrane spanning G protein-linked receptors (chemokine receptors) on target cells. To date, four different such receptors have been identified for the alpha chemokines (Cxcr1-4) and five for the beta chemokines (Ccr1-5). The interaction of chemokines with these receptors causes a rapid reconfiguration of adhesion proteins, such as integrins, on the surface of the respond cells, facilitating their adhesion to endothelial cells (EC) lining blood vessel walls, transmigration between the EC into the tissues and migration along a gradient of increasing concentration of the chemokine to the site of origin. Once at the site of origin, the recruited cells perform their effector functions, such as, but not limited to, production of cytokines. The transmigration and migration may be aided by various molecules that impact tissue remodeling.

The pattern of chemokines and chemokines receptor expression can impact the effectiveness, duration and intensity of the inflammatory response. The data in Table 1 show that the genes encoding the chemokines receptors Ccr6 and Cxcr4 as well as the chemokines Ccl20 and Cxc19 are expressed in a lineage specific manner in Th-17 cells. Furthermore, the genes encoding various polypeptides involved in adhesion (Itga3 and Itga7) and tissue remodeling (Timp1 and Timp2) are also expressed in a lineage specific manner in Th-17 cells. Ccr6 and its ligand Ccl20 are over-expressed 32 folds in Th-17 cells as compared to Th-1 cells. Ccr6, the sole receptor for the chemokine Ccl20, has been associated with the trafficking of subsets of T, B, and dendritic cells to epithelial sites, but has not been previously associated with a specific T cell phenotype or lineage. This association suggests that chemokines and chemokines receptors, such as, but not limited to, Ccl120, Ccr6, Cxcr4, Cxc19, Itga3, Itga7, Timp 1 and Timp2 are involved in migration of Th-17 cells to sites of inflammation and offer therapeutic targets for intervention in disease states that involve Th-17 function.

In addition, it is known that various cytokines, cytokine receptors, signaling molecules and transcription factors also play a key role in the directed development of CD4+ effectors cells, such as Th-1, Th-2 and Th-17 cells. Therefore, the differential expression of such cytokines, cytokine receptors, signaling molecules and transcription factors can provide further insight into the mechanisms for CD4+ effector cell development and offer targets to differentially inhibit or stimulate such development. For example, as discussed herein CD4+ cells differentiate into distinct effector subsets that are characterized by their unique cytokine/cytokine receptor expression and immunoregulatory function. Th-1 cells produce IFN-γ and IL-12, Th-2 cells produce IL-4 and Th-17 cells produce IL-6. These cytokines may be responsible for function of the effector T cells and also be involved in commitment and development of such effector T cells. In Th-17 cells, lineage specific commitment and differentiation is initiated by TGF-B and IL-6 and reinforced by IL-23 (with IL-23 responsiveness being conferred by an up-regulation of IL-23R by TGF-B). In this process, a number of signaling molecules and transcription factors are involved, such as but not limited to, signal transduction and activators of transcription (STAT)3 and retinoic acid receptor-related orphan receptor (ROR)-γ (encoded by the Rorc gene). Th-17 cells produce a number of factors, including, but not limited to, IL-17A/F, IL-21 and IL-22, all of which regulate inflammatory responses by tissue cells.

Table 1 shows that a variety of genes encoding cytokines, cytokine receptors, signaling molecules and transcription factors are expressed in Th-17 cells in a lineage specific manner. These include, but are not limited to, Rorc, Rora, Crem, Wwtr1, Il17a, Il21, Il24, Tnfrs25, Ifngr2, Il1r1, Stat 1, Stat2 and Stat3. Such genes and/or the polypeptide products therefore represent mediators of Th-17 function and offer therapeutic targets for intervention in disease states that involve Th-17 function.

| Gene Class | Gene | Relative Expression |
|---|---|---|
| Transcription factor | Rorc | ++++ |
| | Rora | +++ |
| | Crem | + |
| | Wwtr1 | ++++ |
| Cytokine/Cytokine receptor | Il17a | ++++ |
| | Il21 | + |
| | Il24 | ++ |
| | Tnfrsf25 | + |
| | Ifngr2 | ++++ |
| | Il1r1 | ++ |
| Chemokine/Chemokine receptor | Ccr6 | ++++ |
| | Cxcr4 | + |
| | Cccl20 | ++++ |
| | Cxcl9 | + |
| Adhesion | Itga3 | + |
| | Itga7 | + |
| Tissue remodeling | Timp1 | + |
| | Timp2 | + |
| Signaling | Stat1 | + |
| | Stat3 | + |
| | Socs2 | ++ |

The present disclosure defines a role for TGF-β and/or IL-6 in Th-17 lineage commitment, thereby linking these cytokines to adaptive immunity in a way that has important implications for mechanisms of host defense, immune homeostasis and autoimmunity. Although TGF-(has heretofore been associated primarily with immunosuppressive functions in T-cell immunity, either through the promotion of Treg development and function or inhibition of Th1 and Th2 development, the present disclosure shows that TGF-β may also facilitate pro-inflammatory responses by promoting Th-17 development. These data support a model in which early signaling by TGF-β in an inflammatory context initiates Th-17 commitment and up-regulates IL-23R, providing a basis for TGF-β and IL-23 effects in Th-17 development that parallel those of, and are antagonized by, sequential IFN-γ and IL-12 signaling in Th1 development. The reciprocal and antagonistic actions of TGF-β, IFN-γ and IL-4 on Th-17, Th1 and Th2 development, both through direct actions on the developing T cell and indirectly by modulating cytokine production by innate immune cells, provide an extended mechanism for the efficient matching of effector T-cell polarization, and thus adaptive immunity, to offending pathogens.

Methods

Additional methods are described in 1) Harrington, Nature Immunol., 6:1123 (2005) and 2) Mangan, Nature, 441:231 (2006), and references cited therein.

Mice.

The following mice were purchased from the Jackson laboratories and/or bred in our facility: BALB/cByJ (BALB/c), BALB/c IL-10 deficient, B6.OT-II TCR transgenic mice, B6.129S7-Ifng$^{tm1Ts}$/J (Ifng$^{-/-}$), B6.129S7-Ifngr1$^{tm1Agt}$/J B6.129S1-Il12b$^{tm1Jm}$/J (Il12b$^{-/-}$; also referred to as p40$^{-/-}$), and B6.IL23p19tm (p19$^{-/-}$). DO11.10 TCR transgenic mice (WT), recombination-activating gene 2-deficient DO11.10, STAT1-deficient DO11.10, STAT4-deficient DO11.10 and STAT6 deficient DO11.10 are as described (Ouyang, Immunity, 9, 745 (1998); Ouyang, Immunity 12, 27 (2000); Shinkai, Science 259, 822 (1993); Murphy, Science 250 (1990)). BALB/c T-bet-deficient mice were a gift of D. Bullard and B6 Stat1 −/− mice were provide by R. Lorenz. All animals were housed and treated according to NIH guidelines under the auspices of the UAB IACUC. Spleens from mice homozygous or hemizygous for TGF-β1-deficiency (Tgfb1$^{-/-}$) were a generous gift from Dr. Sharon Wahl.

CD4$^+$ T Cell Isolation and Culture Conditions.

CD4$^+$ T cells from the various strains of mice were purified from pooled spleen and lymph nodes by magnetic sorting using mouse anti-CD4 beads (Dynal-ASA, Oslo, Norway) and the "naïve" fraction isolated by FACS sorting for the CD62L$^+$CD25$^-$ fraction. Cells were plated at a ratio of 1: 5 or 1:8 with bone-marrow-derived dendritic cells in complete medium as described previously (Nature Immunol, Kubo et al., J. Immunol. 173, 7249-7258 (2004)) or irradiated (3000 rads) splenic feeder cells in RPMI 1640 or Iscove's media supplemented with 10% FCS, 2 mM L-glutamine, 1 mM NaPyruvate, 1× non-essential amino acids, 2.5 μM βME, 100 μg/ml penicillin and 100 μg/ml streptomycin (I-10). DO11.10 TCR transgenic CD4+ cells were activated with 5 μM OVA peptide 323-339 (OVAp) whereas non-transgenic cells were stimulated with 2.5 μg/ml anti-CD3 (clone 145-11).

For Th1-polarizing condition, CD4+ T cells were supplemented with IL-12 (10 ng/ml) and anti-IL-4 (10 μg/ml; clone 11B11). For Th-2-polarizing condition, CD4+ T cells were supplemented with recombinant IL-4 (1,000 U/ml) and anti-IL-12 (10 μg/ml; clone C17.8) and anti-IFN-γ (10 μg/ml; cloneXMG1.2).

Where indicated unless otherwise noted, cultures were supplemented with 10 ng/ml rmIL-23 (R&D Systems), 1-5 ng/ml rhTGF-β1 (R&D Systems), 100 U/ml rIFN-γ (R&D Systems), 20 ng/ml rIL-6 (R&D Systems), 20 U/ml rmIL-2 (R&D Systems), 1000 U/ml rIFN-αA/D (Biosource), 10 μg/ml anti-IFNγ mAb (cloneXMG1.2), 10 μg/ml anti-IL-4 mAb (clone 11B11), 10 μg/ml anti-IL-6 mAb (R&D Systems), 10 μg/ml anti-IL-12 mAb (clone C17.8) and 10 μg/ml anti-TGF-β1 mAb (clone 1D11) (R&D Systems). Three days after initiation, cultures were split 1:2 and were further supplemented with IL-2 (50 U/ml; R&D Systems). Cells were harvested on day 6 for analysis.

Colonic lamina propria cells were obtained by a protocol modified from that previously described[25]. Briefly, cecum and colon were removed, opened longitudinally, and washed in HBSS to remove debris. To remove mucous, the tissue was cut into 1 cm pieces and incubated for 30 min at 37° C. with gentle shaking in 1 mM DTT in HBSS containing 2% FCS. A subsequent incubation in 1 mM EDTA in HBSS with 2% FCS for 30 min at 37° C. with gentle shaking was performed to remove epithelium. Tissue was collected, further cut into smaller pieces, and digested with 0.5 mg/ml collagenase type IV (Sigma-Aldrich. St. Louis, Mo.) at 37° C. with gentle shaking for 90-120 min. Lamina propria (LP) cells were harvested by discontinuous 40/75 percoll gradient (Amersham Biosciences. Uppsala, Sweden).

BMDC Cultures

BMDCs were prepared as described and were used on day 12 of culture. For CD4+ T cell activation with BMDCs, purified CD4+ T cells were cultured with irradiated BMDCs at a ratio of 5:1 and cells were stimulated with 2.5 μg/ml of anti-CD-3 (clone 145-2C11) and 10 ng/ml of reconstituted IL-23 with or without 10 μg/ml of anti-IFN-γ (clone XMG1.2)

*Citrobacter rodentium* Inoculation.

*C. rodentium* (ATCC 51459) was prepared by incubation with shaking at 37° C. for 6 hours in LB broth (Invitrogen; Carlsbad, Calif.). After 6 hours, the relative concentration of bacteria was assessed by measuring absorbance at $OD_{600}$ and confirmed by plating of serial dilutions on LB agar. Inoculation of the mice was achieved by oral administration of 1-2× $10^9$ cfu. In anti-TGF-b-treated animals, mice received 1 mg of anti-TGF-β via i.p. injection in saline on d. −1 and d. 4 as previously reported[26]. Tissues were collected for histology and/or cytokine phenotyping at times indicated post inoculation.

Proliferation Assay.

CD4+ T cells activated in Th1 or Th2 polarizing conditions were collected 5 days later, washed and re-stimulated in triplicate with irradiated splenic feeder cells and recombinant IL-2 (50 U/ml) with or without anti-CD-3 (2.5 μg/ml; clone 145-11 and 0, 1, 0r 10 ng/ml or indicated cytokine. Proliferation was assessed 72 hours later with [$^3$H]thymidine added during the final 24 hours.

Flow Cytometric Analysis.

Cells were stimulated for 5-6 h with 50 ng/ml PMA (Sigma) and 750 ng/ml ionomycin (Calbiochem) or not at all. After 1 h, GolgiStop or GolgiPlug (BD Pharmingen, San. Diego, Calif.) was added to block cytokine secretion. Cells were surface stained for 15-30 min at 4° C. with flourescein isothiocynate (FITC)- or PerCP-conjugated anti-CD4 mAb (RM4-5; BD Pharmingen, San Diego, Calif.) or mAB KJI-26 (which recognizes DO11.10 TCR) in PBS supplemented with 1% BSA and 0.2% sodium azide. T cells were fixed and permeabilized with Cytofix/Cytoperm (BD Pharmingen, San Diego, Calif.) and stained intracellular with appropriately labeled-conjugated antibodies to desired cytokines: anti-IL-17 (TC11-18H10) (BD PharMingen, San Diego, Calif.) anti-IL-4 (11B11) and FITC-labeled anti-IFN-γ (XMG1.2) (eBioscience, San Diego, Calif.). For Foxp3 staining, surface stained T cells were incubated in permeabilization buffer (eBioscience, San Diego, Calif.) for 16-18 h at 4° C. before performing intracellular staining with FITC-conjugated anti-Foxp3 (eBioscience, San Diego, Calif.). Samples were acquired on a FACSCalibur flow cytometer and data analysis was conducted using CellQuest Pro software (BD Biosciences, San Diego, Calif.).

RNA Isolation, cDNA Synthesis, and Real-Time RT-PCR.

CD4+ T cells cultured for 6 days under polarizing conditions were re-stimulated with PMA (50 ng/ml; Sigma) and ionomycin (Calbiochem, 750 ng/ml) for 4-6 hours. Cells were lysed and RNA isolated by TRIzol extraction (Invitrogen) and treated with DNA-free (Ambion) according to the manufacturer's directions. First strand synthesis was done using Superscript III (Invitrogen) according to the manufacturer's directions. Real-time, reverse-transcribed PCR (RT-PCR) was conducted on a Bio-Rad iCycleriQ instrument with primer pairs and probes using Platinum Quantitative PCR SuperMix-UDG at a concentration of 1.5× (Invitrogen). The sequences used were as described in Harrington, Nature Immunol., 6:1123 (2005) and Mangan, Nature, 441:231 (2006)). Multiplex reactions were run in duplicate and samples were normalized to the internal control β2-microglobulin. "Fold differences" were calculated with the $\Delta\Delta C^t$ method.

Statistics.

Statistical significance was calculated by unpaired Student's t test or Mann-Whitney U test using Prism software (GraphPad, San Diego, Calif.). All p values 5.0.05 are considered significant, and are referred to as such in the text. Unless otherwise specified, all studies for which data are presented are representative of at least two similar studies.

The foregoing description illustrates and describes the methods and compositions of the present disclosure. Additionally, the disclosure shows and describes only certain embodiments of the methods and compositions but, as mentioned above, it is to be understood that the teachings of the present disclosure are capable of use in various other combinations, modifications, and environments and is capable of changes or modifications within the scope of the inventive concept as expressed herein, commensurate with the above teachings and/or the skill or knowledge of the relevant art. The embodiments described hereinabove are further intended to explain best modes known of practicing the invention and to enable others skilled in the art to utilize the invention in such, or other, embodiments and with the various modifications required by the particular applications or uses of the invention. Accordingly, the description is not intended to limit the invention to the form disclosed herein. All patent and literature references cited herein are incorporated by reference as if fully set forth in this disclosure.

What is claimed is:

1. A method of inhibiting the generation of a Th-17 effector cell, said method comprising the step of:
   a. exposing a Th-17 effector cell precursor to an antagonist of interleukin-23 (IL-23) function thereby inhibiting the generation of the Th-17 effector cell;
   b. exposing a Th-17 effector cell precursor to an antagonist of transforming growth factor-beta (TGF-β) function, an antagonist of interleukin-6 (IL-6) function, an antagonist of interleukin-17 (IL-17) function or a combination of the foregoing; and
   c. exposing the Th-17 effector cell precursor to an effective amount of an agent that inhibits Th-17 effector cell activity.

2. The method of claim 1, wherein the antagonist of IL-23 function inhibits the commitment of Th-17 effector cell precursor to a Th-17 developmental pathway, inhibits the development of Th-17 effector cell precursor that is committed to a Th-17 developmental pathway, inhibits the maintenance of a Th-17 developmental pathway, inhibits the survival of cells committed to a Th-17 developmental pathway, inhibits the activity of cells committed to a Th-17 developmental pathway or a combination of the foregoing.

3. The method of claim 1, wherein the antagonist is an antibody to IL-23, an antibody to the IL-23 receptor, a soluble form of the IL-23 receptor, an oligopeptide that binds IL-23 or the IL-23 receptor, an IL-23 receptor antagonist, a polynucleotide that reduces the expression of IL-23 or the IL-23 receptor, or an organic molecule.

4. The method of claim 1, wherein the antagonist inhibits the stimulatory activity of IL-23 on the generation the Th-17 effector cell.

5. The method of claim 1, wherein the agent is interleukin-12 (IL-12), an IL-12 agonist, interferon-beta (IFN-β), an agonist of IFN-β, interferon-gamma (IFN-γ), an agonist of IFN-γ, interferon-alpha (IFN-α), an agonist of IFN-α, interleukin-4 (IL-4), an agonist of IL-4 or a combination of the foregoing.

* * * * *